US012735722B2

(12) United States Patent
Delgoffe et al.

(10) Patent No.: US 12,735,722 B2
(45) Date of Patent: Sep. 15, 2026

(54) ONCOLYTIC VIRUSES ENCODING RECOMBINANT TRANSFORMING GROWTH FACTOR (TGF)-BETA MONOMERS AND USES THEREOF

(71) Applicant: University of Pittsburgh—Of the Commonwealth System of Higher Education, Pittsburgh, PA (US)

(72) Inventors: Greg M. Delgoffe, Pittsburgh, PA (US); Andrew P. Hinck, Pittsburgh, PA (US); Kristin DePeaux, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 634 days.

(21) Appl. No.: 18/022,936

(22) PCT Filed: Aug. 27, 2021

(86) PCT No.: PCT/US2021/048043
§ 371 (c)(1),
(2) Date: Feb. 23, 2023

(87) PCT Pub. No.: WO2022/047220
PCT Pub. Date: Mar. 3, 2022

(65) Prior Publication Data

US 2024/0011046 A1 Jan. 11, 2024

Related U.S. Application Data

(60) Provisional application No. 63/070,965, filed on Aug. 27, 2020.

(51) Int. Cl.

| | |
|---|---|
| ***C12N 15/86*** | (2006.01) |
| ***A61K 35/768*** | (2015.01) |
| ***A61P 35/00*** | (2006.01) |
| ***C07K 14/495*** | (2006.01) |

(52) U.S. Cl.
CPC ............ *C12N 15/86* (2013.01); *A61K 35/768* (2013.01); *A61P 35/00* (2018.01); *C07K 14/495* (2013.01)

(58) Field of Classification Search
None
See application file for complete search history.

(56) References Cited

U.S. PATENT DOCUMENTS

| | | | |
|---|---|---|---|
| 7,208,313 | B2 | 4/2007 | McCart et al. |
| 2005/0203037 | A1 | 9/2005 | Chu et al. |
| 2019/0359667 | A1 | 11/2019 | Hinck et al. |
| 2020/0087411 | A1 | 3/2020 | Kley et al. |

FOREIGN PATENT DOCUMENTS

| | | | |
|---|---|---|---|
| WO | WO 2018/094173 | 5/2018 | |
| WO | WO-2018094173 A1 * | 5/2018 | ........... C07K 14/495 |
| WO | WO 2019/148109 | 8/2019 | |
| WO | WO 2021/081258 | 4/2021 | |

OTHER PUBLICATIONS

Akhurst, "Targeting TGF-β Signaling for Therapeutic Gain," *Cold Spring Harb Perspect Biol.*, 2017;9, 32 pages.
Hinck et al., "Structural Biology and Evolution of the TGF-β Family," *Cold Spring Harb Perspect Biol.*, 2016;8, 53 pages.
Huang et al., "Production, Isolation, and Structural Analysis of Ligands and Receptors of the Tgf-β Superfamily," *Methods Mol. Biol.*, vol. 1344:63-92, 2016.
International Search Report and Written Opinion of PCT/US2021/048043, mailed Feb. 9, 2022 (11 pages).
Kim et al., "An Engineered Transforming Growth Factor β (TGF-β) Monomer that Functions as a Dominant Negative to Block TGF-β Signaling," *J. Biol. Chem.*, vol. 292:7173-7188, 2017.
McCart et al., "Systemic Cancer Therapy with a Tumor-selective Vaccinia Virus Mutant Lacking Thymidine Kinase and Vaccinia Growth Factor Genes," *Cancer Res.*, vol. 61:8751-8757, 2001.
Raja et al., "Oncolytic Virus Immunotherapy: Future Prospects for Oncology," *J. ImmunoTher Cancer*, vol. 6:140, 2018 (13 pages).
Zheng et al., "Oncolytic Viruses for Cancer Therapy: Barriers and Recent Advances," *Mol. Ther. Oncolytics*, vol. 15:234-247, 2019.

* cited by examiner

*Primary Examiner* — Tracy Vivlemore
*Assistant Examiner* — Catherine L McCormick
(74) *Attorney, Agent, or Firm* — Klarquist Sparkman, LLP

(57) ABSTRACT

Oncolytic viruses encoding a recombinant form of TGF-β engineered to prevent homodimerization and recruitment of TGF-β receptor I are described. The engineered TGF-β monomers function as dominant-negative TGF-β inhibitors. Oncolytic viruses encoding a TGF-β monomer can be used for cancer immunotherapy to inhibit the immunosuppressive tumor microenvironment.

23 Claims, 16 Drawing Sheets

Specification includes a Sequence Listing.

FIG. 1A

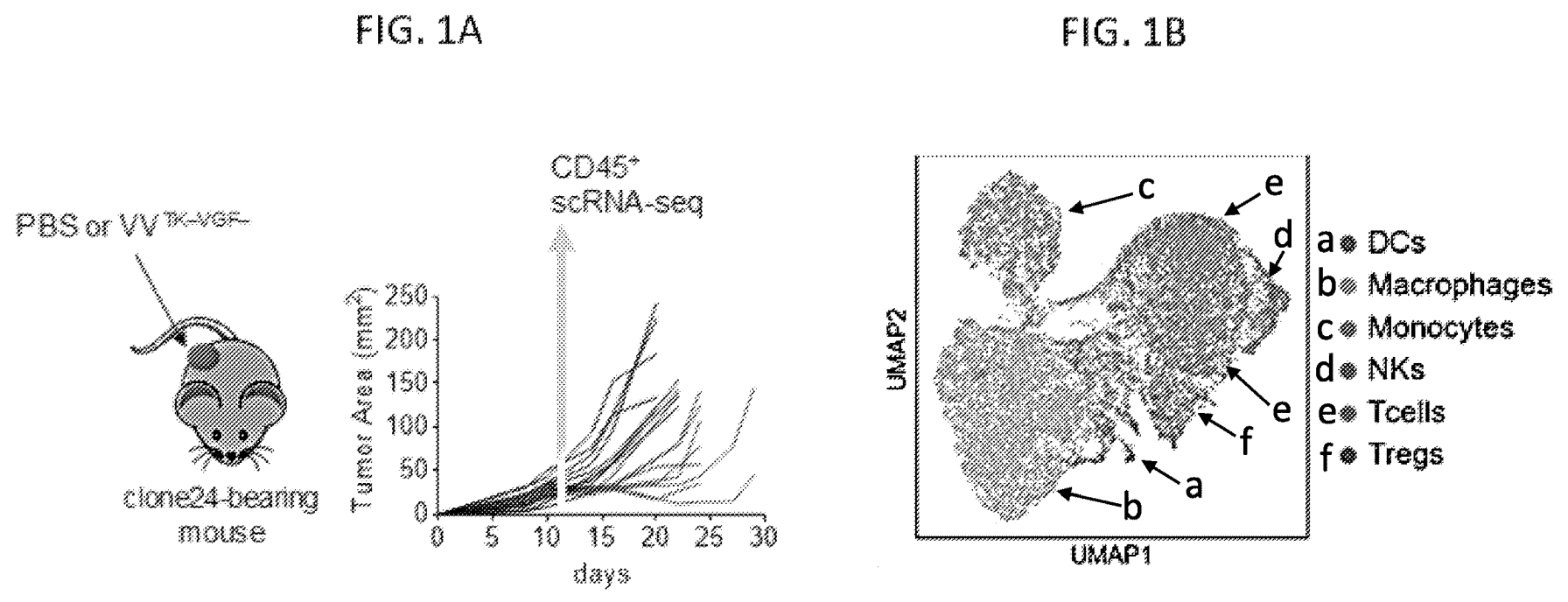

PBS or $VV^{TK-VGF-}$
clone24-bearing mouse
CD45$^{+}$ scRNA-seq
Tumor Area ($mm^2$)
0 50 100 150 200 250
0 5 10 15 20 25 30
days

FIG. 1B a DCs
b Macrophages
c Monocytes
d NKs
e Tcells
f Tregs
UMAP1
UMAP2

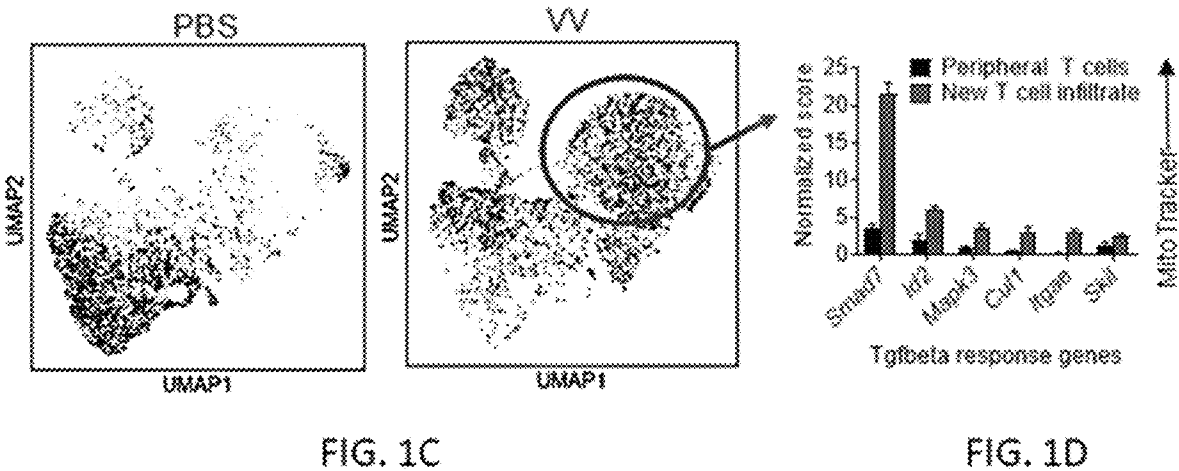
FIG. 1C
FIG. 1D
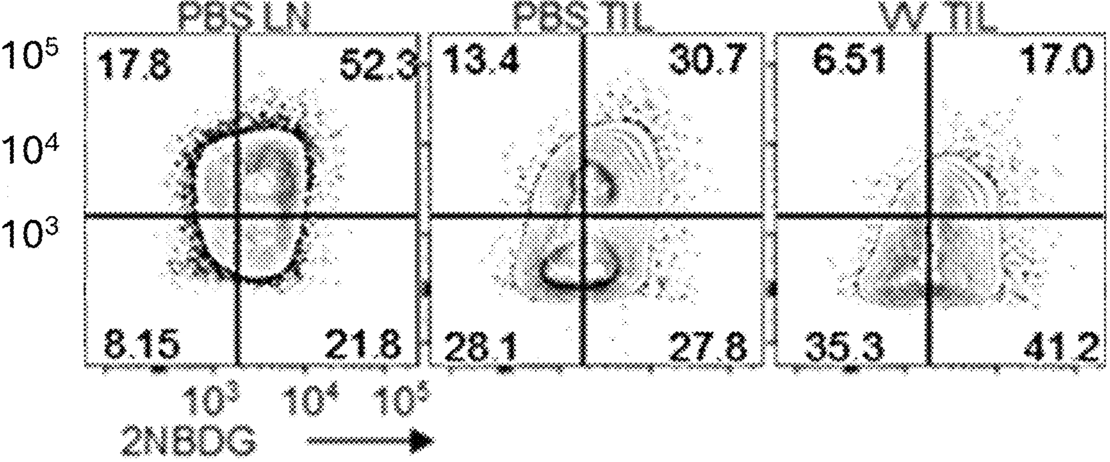
FIG. 1E

Engineered Ligand

Ligand

1

2

I

II

Relative Luciferase Response
TGF-β1
mTGF-β3
mmTGF-β2-7M
log10 (Molar Concentration)
Stimulation with 8 pM TGF-β1
mTGF-β3
mmTGF-β2-7M
log10 ( Molar Concentration)
Stimulation with 10 pM TGF-β2
IC50 = 19 ± 3 nM
Log([mmTGFβ2-7m])
Stimulation with 10 pM TGF-β3
IC50 = 21 ± 8 nM
Log([mmTGFβ2-7m])

FIG. 3A
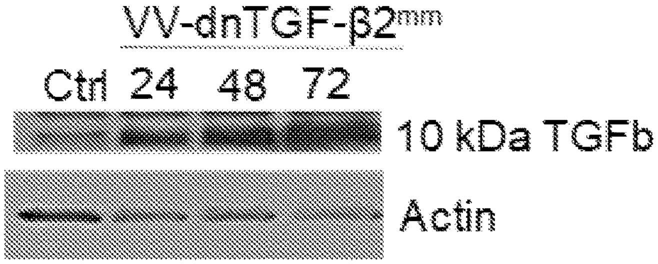
FIG. 3B
FIG. 3C
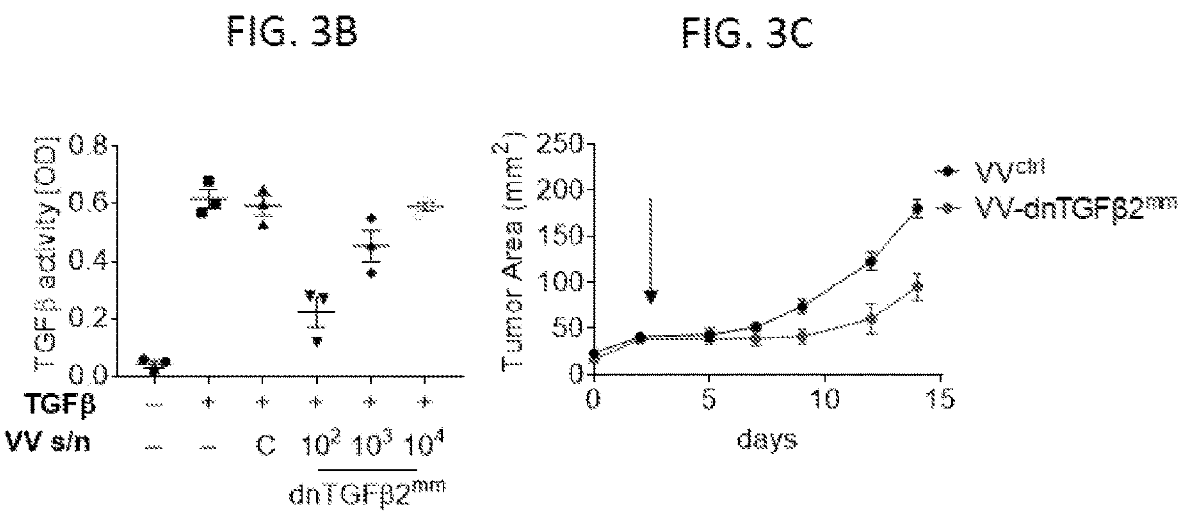

FIG. 4A

TGF-β2 (SEQ ID NO: 2) vs. mmTGF-β2-7M (SEQ ID NO: 7)

1. Heel Helix Deletion
2. Substitution of cysteine at interchain disulfide position with serine
3. Introduction of Basic Residues in Heel Helix region
4. Seven Modifications that partially convert TGF-β2 sequence into TGF-β1

```
SEQ ID NO: 2  ALDAAYCFRNVQDNCCLRPLYIDFKRDLGWKWIHEPKGYNANFCAGACPYLWSSDTQHT  59
SEQ ID NO: 7  ALDAAYCFRNVQDNCCLRPLYIDFRKDLGWKWIHEPKGYNANFCAGACPYR--------  51
              ************************44************************311111111

SEQ ID NO: 2  KVLSLYNTINPEASASPCCVSQDLEPLTILYYIGNTPKIEQLSNMIVKSCKCS  112
SEQ ID NO: 7  ------------ASKSPSCVSQDLEPLTIVYYVGRKPKVEQLSNMIVKSCKCS  92
              111111111111**3**2***********4**4*44**4**************
```

TGF-β3-(TβRII)$_2$-(TβRI)$_2$

TGF-β3-TβRII

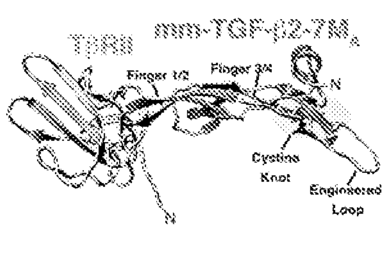

mmTGF-β2-7M (SEQ ID NO: 7) vs mmTGF-β2-7M2R (SEQ ID NO: 9)

5. Substitution of interchain disulfide position with arginine
6. Introduction of Basic Residue at dimer interface

```
                                                                     57 59
SEQ ID NO: 7  ALDAAYCFRNVQDNCCLRPLYIDFRKDLGWKWIHEPKGYNANFCAGACPYRASKSPSCV  59
SEQ ID NO: 9  ALDAAYCFRNVQDNCCLRPLYIDFRKDLGWKWIHEPKGYNANFCAGACPYRASKSPrCr  59
              ********************************************************5*6

SEQ ID NO: 7  SQDLEPLTIVYYVGRKPKVEQLSNMIVKSCKCS  92
SEQ ID NO: 9  SQDLEPLTIVYYVGRKPKVEQLSNMIVKSCKCS  92
              *********************************
```

FIG. 4B

FIG. 4C mmTGF-β2-7M ( SEQ ID NO: 7 ) vs mmTGF-β2-2M-Del8-17 ( SEQ ID NO: 10 )

7. Elimination of cysteines that form the 8-17 disulfide
8. Modifications that revert TGF-β1 sequence back to TGF-β2

```
                   7        16
                   |        |
SEQ ID NO: 7   ALDAAYCFRNVQDNCCLRPLYIDFRKDLGWKWIHEPKGYNANFCAGACPYRASKSPSCV  59
SEQ ID NO: 10  ALDAAYVFRNVQDNCALRPLYIDFRRDLGWKWIHEPKGYNANFCAGACPYRASKSPSCV  59
               ******7********7*********8*********************************

SEQ ID NO: 7   SQDLEPLTIVYYVGRKPKVEQLSNMIVKSCKCS  92
SEQ ID NO: 10  SQDLEPLTILYYIGRTPKIEQLSNMIVKSCKCS  92
               *********8**8**8**8**************
```

mmTGF-β2-7M ( SEQ ID NO: 7) vs mmTGF-β2-7M-PRDC ( SEQ ID NO: 11 )

9. Modification due to grafting with cystine-knot region of PRDC

```
                                        Finger 1-2
SEQ ID NO: 7   ---------ALDAAYCFRNVQDNCCLRPLYIDFRKDLGWKWIHEPKGYNANFCAGACPY  50
SEQ ID NO: 11  KEVLASSQEALVVTERKYLKSDWCKLRPLYIDFRKDLGWKWIHEPKGYNANFCYGQCNS  59
               999999999**999999999*9*9*****************************9*9*99
                                   Finger 3-4
SEQ ID NO: 7   R------------ASKSPSCVSQDLEPLTIVYYVGRKPKVEQLSNMIVKSCKCS--  92
SEQ ID NO: 11  FYIPRHVKKEEDSFQSSAFCVSQDLEPLTIVYYVGRKPKVEQLSNMIVKSCRCMSV  115
               999999999999999999*********************************9*999
```

FIG. 4D

FIG. 4E mmTGF-β2-7M (SEQ ID NO: 7) vs mmTGF-β2-7M2R-Del8-17 *or* var1 (SEQ ID NO: 12)

```
5. Substitution of interchain disulfide position with arginine
6. Introduction of Basic Residue at dimer interface
7. Elimination of cysteines that form the 8-17 disulfide
                    7        16
                    |        |
SEQ ID NO: 7   ALDAAYCFRNVQDNCCLRPLYIDFRKDLGWKWIHEPKGYNANFCAGACPYRASKSPSCV   59
SEQ ID NO: 12  ALDAAYVFRNVQDNCALRPLYIDFRKDLGWKWIHEPKGYNANFCAGACPYRASKSPrCr   59
               ******7********7****************************************5*6

SEQ ID NO: 7   SQDLEPLTIVYYVGRKPKVEQLSNMIVKSCKCS   92
SEQ ID NO: 12  SQDLEPLTIVYYVGRKPKVEQLSNMIVKSCKCS   92
               *********************************
```

pH 4.6 pH 7.2 pH 7.2 (10 mM CHAPS)
mmTGFβ2-7M2R mmTGFβ2-7M
15N (ppm)
1H (ppm)

pH 4.8
105
110
115
120
125
130
15N (ppm)
9.5 9 8.5 8 7.5 7 6.5
1H (ppm)

pH 6.0
105
110
115
120
125
130
15N (ppm)
9.5 9 8.5 8 7.5 7 6.5
1H (ppm)
pH 6.0
105
110
115
120
125
130
15N (ppm)
9.5 9 8.5 8 7.5 7 6.5
1H (ppm)

TβRII + + + + + +
7M +B +A
7M2R +A +B
7M-PRDC +B
Ratios: A ~ 1:1, B ~ 2:1

| | ΔG [kcal/mol] | ΔH [kcal/mol] | ΔS [cal/mol•K] | $K_D$ [nM] | $K_D$ (range) |
|---|---|---|---|---|---|
| mmTGF-β2-7M | -9.846 | -4.631 | 17.491 | 60.5 | 5.5-413.3 |
| mmTGF-β2-7M2R | -10.05 | -10.485 | -1.44 | 75.1 | 38.7-132.1 |
| mmTGF-β2-2M-Del8-17 | -10.001 | -7.670 | -7.566 | 80.1 | 56.4-113.1 |

FIG. 9A $IC_{50}$ = 58.23 nM
mmTGF-β2-7M nM 7m

FIG. 9B $IC_{50}$ = 53.29 nM
mmTGF-β2-7M2R nM 7m2r

FIG. 9C $IC_{50}$ = 111.0 nM
mmTGF-β2-2M-Del8-17 nM 7m var 1

Figures 9A, 9B, 9C, 9D:
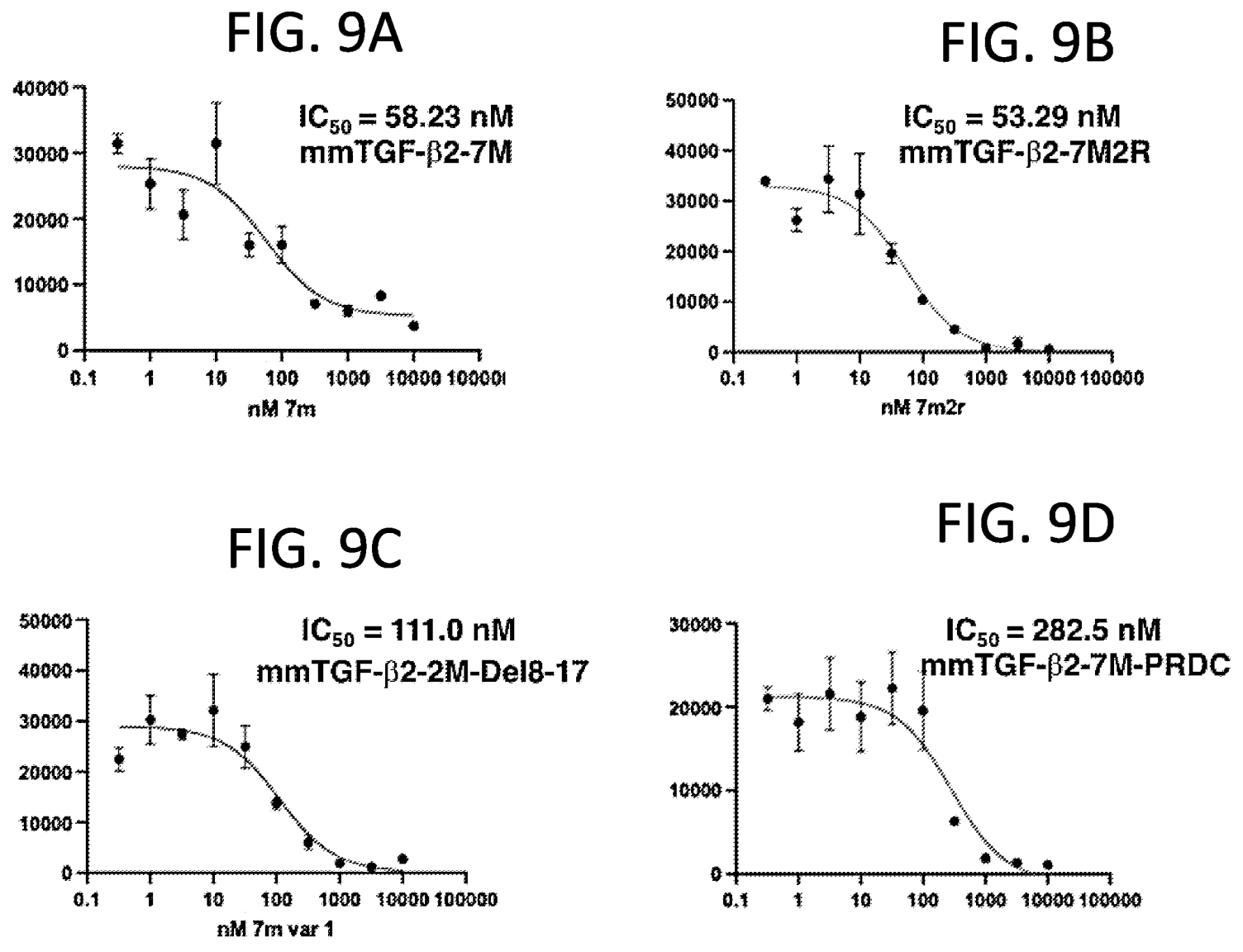

FIG. 9D $IC_{50}$ = 282.5 nM
mmTGF-β2-7M-PRDC

CL24 melanoma (Pten-deficient $Braf^{V600E}$)

ONCOLYTIC VIRUSES ENCODING RECOMBINANT TRANSFORMING GROWTH FACTOR (TGF)-BETA MONOMERS AND USES THEREOF

CROSS REFERENCE TO RELATED APPLICATIONS

This application is the U.S. National Stage of International Application No. PCT/US2021/048043, filed Aug. 27, 2021, which was published in English under PCT Article 21(2) which claims the benefit of U.S. Provisional Application No. 63/070,965, filed Aug. 27, 2020. The above-listed applications are herein incorporated by reference in their entirety.

ACKNOWLEDGMENT OF GOVERNMENT SUPPORT

This invention was made with government support under grant numbers GM058670 and CA172886 awarded by the National Institutes of Health. The government has certain rights in the invention.

FIELD

This disclosure concerns oncolytic viruses encoding recombinant TGF-β monomers, which function as TGF-β signaling inhibitors. This disclosure further concerns use of the TGF-β monomer-encoding oncolytic viruses for cancer immunotherapy.

INCORPORATION OF ELECTRONIC SEQUENCE LISTING

The electronic sequence listing, submitted herewith as a .txt file named 103782-11_ST25.txt (11,167 bytes), created on Feb. 22, 2023, is herein incorporated by reference in its entirety.

BACKGROUND

TGF-β is a multifunctional cytokine with diverse biological effects on cellular processes, including cell proliferation, migration, differentiation, and apoptosis. The three mammalian TGF-β isoforms, TGF-β1, -β2 and -β3, exert their functions through a cell surface receptor complex composed of type I (TβRI) and type II (TβRII) serine/threonine kinase receptors. Receptor activation induces both SMAD proteins and other downstream targets, including Ras, RhoA, TAK1, MEKK1, PI3K, and PP2A, to produce the full spectrum of TGF-β responses (Roberts and Wakefield, *Proc Natl Acad Sci USA* 100:8621-8623, 2003; Derynck and Zhang, *Nature* 425:577-584, 2003; Massagué, *Cell* 134:215-230, 2008).

SUMMARY

Oncolytic viruses encoding transforming growth factor (TGF)-β monomers engineered to prevent homodimerization and signaling are disclosed. Recombinant engineered monomeric TGF-β functions as an inhibitor of TGF-β signaling by preventing recruitment of TORI and thereby blocking downstream signaling. Oncolytic virus, such as vaccinia virus, encoding monomeric TGF-β can be used, for example, as a cancer immunotherapeutic.

Provided are oncolytic viruses encoding a recombinant TGF-β monomer, such as a human recombinant TGF-β monomer. The TGF-β monomer includes a cysteine to serine substitution (or alternatively, a cysteine to arginine substitution) at an amino acid residue corresponding to residue 77 of human TGF-β2 (set forth herein as SEQ ID NO: 2) and a deletion of the α3 helix corresponding to amino acid residues 52-71 of human TGF-β2. The TGF-β monomer can be, for example, a human TGF-β1, human TGF-β2 or human TGF-β3 monomer.

In some embodiments, the TGF-β monomer is a human TGF-β2 monomer that further includes a leucine to arginine substitution at an amino acid residue corresponding to residue 51 of human TGF-β2 and/or an alanine to lysine substitution at an amino acid residue corresponding to residue 74 of human TGF-β2. In other embodiments, the TGF-β monomer is a human TGF-β1 monomer that further includes an isoleucine to arginine substitution at an amino acid residue corresponding to residue 52 of human TGF-β1 (set forth herein as SEQ ID NO: 1); an alanine to lysine substitution at an amino acid residue corresponding to residue 74 of human TGF-β1; and/or an alanine to serine substitution at an amino acid residue corresponding to residue 75 of human TGF-β1. In other embodiments, the TGF-β monomer is a human TGF-β3 monomer that further includes a leucine to glutamate substitution at an amino acid residue corresponding to residue 51 of human TGF-β3 (set forth herein as SEQ ID NO: 3); an alanine to glutamate substitution at an amino acid residue corresponding to residue 72 of human TGF-β3; and/or an alanine to aspartate substitution at an amino acid residue corresponding to residue 74 of human TGF-β3. In some examples, the TGF-β monomer further includes at least one amino acid substitution that increases affinity of the monomer for TβRII. In some examples, the monomer further includes at least one amino acid substitution that decreases aggregation of the monomer. In some examples, the monomer further includes at least one amino acid substitution that improves folding of the monomer.

In alternative embodiments, provided is an oncolytic virus encoding a human recombinant TGF-β2 monomer modified to include the cystine-knot region of protein related to Dan and Cerubus (PRDC). In some examples, the amino acid sequence of the TGF-β2 monomer comprises or consists of SEQ ID NO: 11.

In some embodiments, the oncolytic virus is a vaccinia virus (VV), a herpes simplex virus (HSV), or an adenovirus.

Also provided are compositions that include an oncolytic virus encoding a human recombinant TGF-β monomer disclosed herein and a pharmaceutically acceptable carrier.

Further provided are methods of treating cancer in a subject, and methods of inhibiting tumor growth or metastasis in a subject with cancer, by administering to the subject a therapeutically effective amount of an oncolytic virus disclosed herein. In some embodiments, the cancer is melanoma, head and neck cancer, or pancreatic cancer.

The foregoing and other objects and features of the disclosure will become more apparent from the following detailed description, which proceeds with reference to the accompanying figures.

BRIEF DESCRIPTION OF THE DRAWINGS

FIGS. 1A-1E: Single-cell RNA sequencing (scRNA-seq) reveals oncolytic virus induces dramatic immune infiltration that succumbs to metabolic and immunologic suppression. (FIG. 1A) Experimental setup. Pten-deficient, Braf$^{V600E}$ clone24 melanoma-bearing mice were treated with either PBS or oncolytic double-deleted (TK- and VGF-deleted)

VV. An example tumor growth curve is shown. At day 12, when tumors had not yet regressed, CD45+ cells were subjected to scRNA-seq. (FIG. 1B) Uniform Manifold Approximation and Projection (UMAP) clustering of all cells sequenced from both treatment groups. (FIG. 1C) UMAP of cells as broken down by treatment, revealing VV induces dramatic tumor microenvironment remodeling. The circle indicates new tumor infiltrating T cells. (FIG. 1D) TGF-β response genes in the new T cell infiltrate. (FIG. 1E) Mitochondrial mass measurements in PBS or VV-treated tumors, indicating CD8+ T cells still succumb to metabolic insufficiency.

Figure 2A:
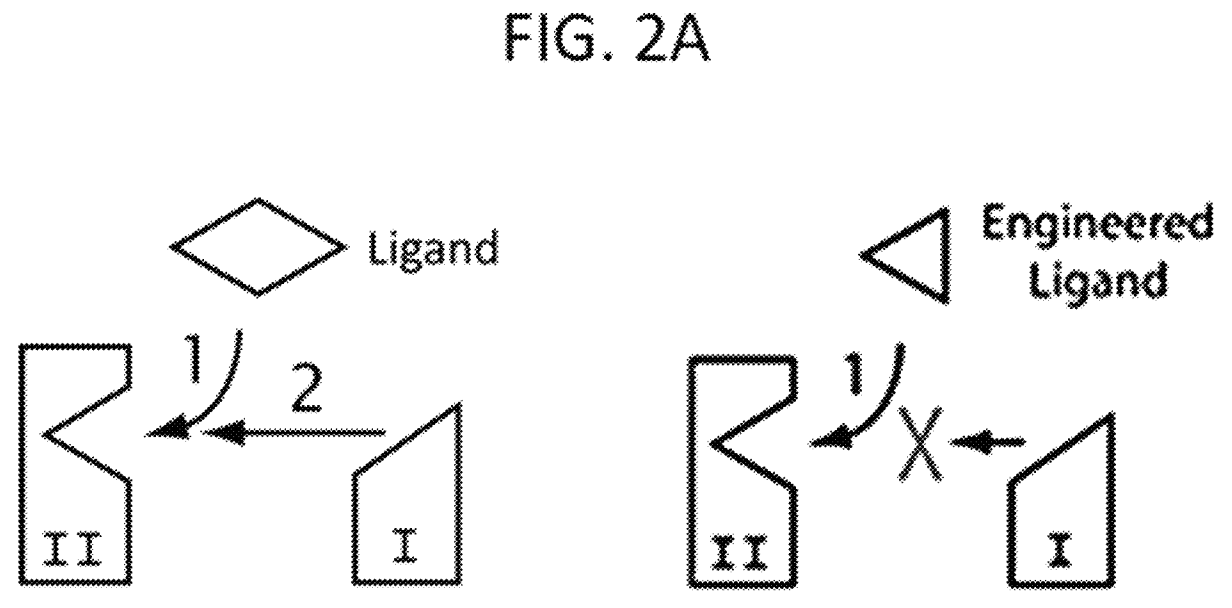

FIGS. 2A-2B: An engineered mini-monomer of TGF-β2 acts as a dominant negative inhibitor of TGFβR signaling. (FIG. 2A) Scheme of how mini-monomeric TGF-β functions. Unmodified TGF-β acts as a dimer and recruits TβRI and TβRII to transduce signals (left). Mutating disulfide bridge-sustaining cysteine residues, and structure-guided removal of critical 'heel' helix that contacts RI, generates a mini-monomeric TGF-β that retains the capacity to bind TGFβRII, but prevents RI recruitment (right). (FIG. 2B) Luciferase assays in a HEK-293 TGF reporter cell line treated with various concentrations of TGF-β1, TGF-β3 or the mini-monomeric molecule (mmTGF-β2-7M, also referred to as dnTGFβ$2^{mm}$), which reveal that dnTGFβ$2^{mm}$ can inhibit the activity of TGF-β1, TGF-β2 and TGF-β3.

FIGS. 3A-3C: dnTGFβ$2^{mm}$ can be delivered by oncolytic virus and has superior anti-tumor activity. (FIG. 3A) Immunoblot for TGF-β in B16 melanoma cells infected with a control virus or VV-dnTGFβ$2^{mm}$ for 24, 48 or 72 hours. A non-reducing gel shows a band at 10 kDa, the approximate size of the mini-monomer. (FIG. 3B) TGF-β reporter assay using recombinant TGF-β and supernatants from control (C) or dnTGFβ$2^{mm}$-expressing virus-infected cells at 10-fold dilutions. (FIG. 3C) Tumor growth curve of B16 melanoma treated with 2.5×10 6 PFU of $VV^{ctrl}$ or engineered dnTGFβ$2^{mm}$ expressing VV.

FIGS. 4A-4E: Sequence comparison of engineered TGF-β monomer mmTGF-β2-7M (SEQ ID NO: 7) to TGF-β2 (SEQ ID NO: 2) (FIG. 4A), mmTGF-β2-7M2R (SEQ ID NO: 9) (FIG. 4B), mmTGF-β2-2M-De18_17 (SEQ ID NO: 10) (FIG. 4C), mmTGF-β2-7M-PRDC (SEQ ID NO: 11) (FIG. 4D), and mmTGF-β2-7M2R-De18-17 (SEQ ID NO: 12) (FIG. 4E). Sequence differences are indicated by numerals under the two aligned sequences, with the identity of the numeral indicating the nature of the difference. Sequence identities are indicated by an asterisk. Shown below the sequences in FIG. 4A is the structure of the TGF-β3-$(T\beta RII)_2$-$(T\beta RI)_2$ complex (PDB 2PJY) (left) and the mmTGF-β2-7M-TβRII complex (PDB 5TX4) (right), with some of the main structural features indicated.

FIG. 7B and FIG. 7C differ only in the contour level at which the signals are plotted (FIG. 7B is plotted at a contour level closer to the noise compared to panel FIG. 7C). Native gel shown in FIG. 7 D was performed by running either 2 μg of TβRII alone (left most lane) or with the engineered TGF-β monomers added in the specified molar ratio (+A and +B indicate TβRII:engineered TGF-β monomer in either a 1:1 or 2:1 molar ratio, respectively).

FIGS. 9A-9D: HEK-293 cell-based CAGA-Luc TGF-β reporter assay to assess inhibitory potency of the engineered TGF-beta monomers relative to one another. HEK-293 cells stably transfected with the TGF-β CAGA-Luc reporter were treated with the indicated engineered TGF-beta monomers at the concentrations specified for 30 minutes and then stimulated by the addition of 10 pM TGF-β3. Cells were harvested after 14 hours and assayed for luciferase activity. (FIG. 9A) mmTGF-β2-7M (SEQ ID NO: 7), $IC_{50}$ of 58.23 nM. (FIG. 9B) mmTGF-β2-7M2R (SEQ ID NO: 9), $IC_{50}$ of 53.29 nM. (FIG. 9C) mmTGF-β2-2M-De18-17 (SEQ ID NO: 10), $IC_{50}$ of 111.0 nM. (FIG. 9D) mmTGF-β2-7M-PRDC (SEQ ID NO: 11), $IC_{50}$ of 282.5 nM. Data points and error bars shown correspond to the mean and standard deviation of triplicate measurements. Smooth curve corresponds to the fit to a standard dose response inhibition isotherm. Fitted $IC_{50}$ values are shown.

(FIG. 10A) C57/BL6J mice were inoculated with the head and neck squamous cell carcinoma (HNSCC) line MEER subclone. At day 7, mice received an intratumoral injection of 2.5×10 5 PFU of either control VV ($VV^{ctrl}$) or VV engineered to express mmTGF-β2-7M2R-De18-17 (labelled as $VV^{mmTGF\beta(var\ 1)}$ or $VV^{mmTGF\beta i}$) (SEQ ID NO: 12). While the control virus had a modest curative effect, half of the mice treated with $VV^{mmTGF\beta(var\ 1)}$ exhibited a complete response and a long lasting survival benefit. (FIG. 10B) C57/BL6J mice were inoculated with the melanoma line clone 24 (CL24). At day 7, mice received $2.5\times10^5$ PFU of VV control ($VV^{Ctrl}$) or VV expressing mmTGFrβi. Administration of $VV^{mmTGF\beta i}$ led to a complete response in 40% of treated animals. (FIG. 10C) Addition of anti-PD1 enhanced the tumor inhibition effect of $VV^{mmTGF\beta i}$ in the CL24 model.

SEQUENCE LISTING

Figure 2B:
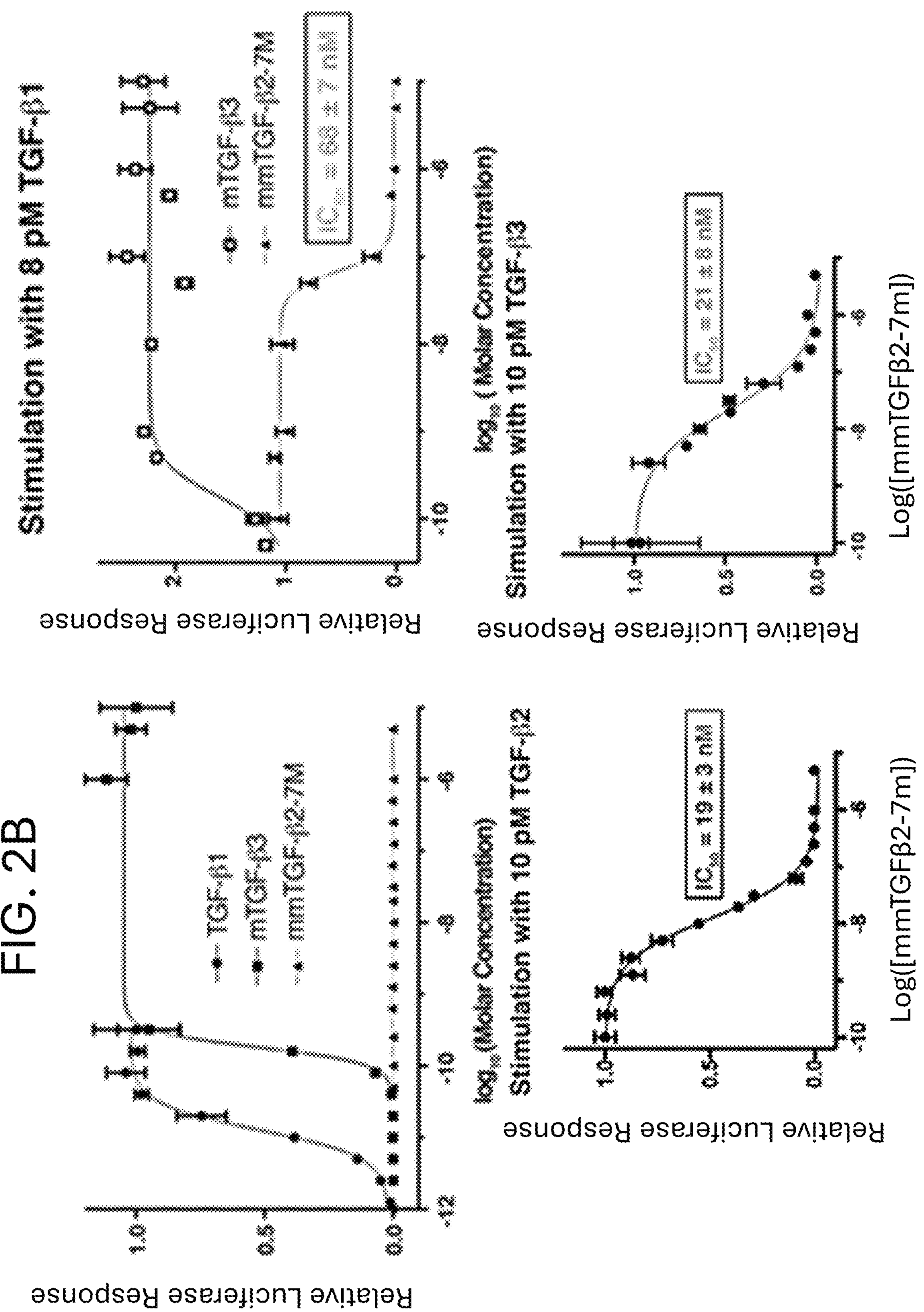

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the amino acid sequence of wild-type human TGF-β1.

SEQ ID NO: 2 is the amino acid sequence of wild-type human TGF-β2.

SEQ ID NO: 3 is the amino acid sequence of wild-type human TGF-β3.

SEQ ID NO: 4 is the amino acid sequence of an engineered human TGF-β1 monomer designated mmTGF-β1.

SEQ ID NO: 5 is the amino acid sequence of an engineered human TGF-β2 monomer designated mmTGF-β2.

SEQ ID NO: 6 is the amino acid sequence of an engineered human TGF-β3 monomer designated mmTGF-β3.

SEQ ID NO: 7 is the amino acid sequence of an engineered human TGF-β2 monomer designated mmTGF-β2-7M.

SEQ ID NO: 8 is the amino acid sequence of the human IL-2 signal sequence.

SEQ ID NO: 9 is the amino acid sequence of an engineered human TGF-β2 monomer designated mmTGF-β2-7M2R.

SEQ ID NO: 10 is the amino acid sequence of an engineered human TGF-β2 monomer designated mmTGF-β2-2M-De18-17.

SEQ ID NO: 11 is the amino acid sequence of an engineered human TGF-β2 monomer designated mmTGF-β2-7M-PRDC.

SEQ ID NO: 12 is the amino acid sequence of an engineered human TGF-β2 monomer designated mmTGF-β2-7M2R-De18-17.

DETAILED DESCRIPTION

I. Abbreviations

CHAPS 3[(3-cholamidopropyl)ditmethylammino]-1-propanesulfonate

CKGF cystine knot growth factor fold

HNSCC head and neck squamous cell carcinoma

HSQC heteronuclear single-quantum correlation

NMR nuclear magnetic resonance oVV oncolytic vaccinia virus

PRDC protein related to Dan and Cerubus scRNA-seq single-cell RNA sequencing

TGF-β transforming growth factor β

TβRI transforming growth factor-β type 1 receptor

TβRII transforming growth factor-β type 2 receptor

TK thymidine kinase

VGF virus growth factor

VV vaccinia virus

II. Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting.

To facilitate review of the various embodiments, the following explanations of terms are provided:

Administration: To provide or give a subject an agent, such as a therapeutic agent (e.g. oncolytic virus encoding TGF-β monomer), by any effective route. Exemplary routes of administration include, but are not limited to, injection or infusion (such as intratumoral, subcutaneous, intramuscular, intradermal, intraperitoneal, intrathecal, intravenous, intraprostatic, intracerebroventricular, intrastriatal, intracranial and into the spinal cord), oral, intraductal, sublingual, rectal, transdermal, intranasal, vaginal and inhalation routes.

Heterologous: Originating from a separate genetic source or species.

Isolated: An "isolated" biological component, such as a nucleic acid, protein (including antibodies), organelle, or recombinant virus, has been substantially separated or purified away from other biological components in the environment (such as a cell) in which the component occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids or proteins. Isolated does not require absolute purity, and can include protein, peptide, nucleic acid molecules or viruses that are at least 50% isolated, such as at least 75%, 80%, 90%, 95%, 98%, 99%, or even 99.9% isolated.

Melanoma: A form of cancer that originates in melanocytes (cells that make the pigment melanin). Melanocytes are found primarily in the skin, but are also present in the bowel and eye. As used herein, "melanoma" refers to any stage of melanoma, or any subtype of melanoma, such as superficial spreading melanoma, nodular melanoma, acral lentiginous melanoma, lentigo maligna, melanoma-in-situ, mucosal melanoma and uveal melanoma.

Modification: A change in the sequence of a nucleic acid or protein sequence. For example, amino acid sequence modifications include, for example, substitutions, insertions and deletions, or combinations thereof. Insertions include amino and/or carboxyl terminal fusions as well as intrasequence insertions of single or multiple amino acid residues. Deletions are characterized by the removal of one or more amino acid residues from the protein sequence. In some embodiments herein, the modification (such as a substitution, insertion or deletion) results in a change in function, such as a reduction or enhancement of a particular activity of a protein. Substitutional modifications are those in which at least one residue has been removed and a different residue inserted in its place. Amino acid substitutions are typically of single residues, but can occur at a number of different locations at once. Substitutions, deletions, insertions or any combination thereof may be combined to arrive at a final mutant sequence. These modifications can be prepared by modification of nucleotides in the DNA encoding the protein, thereby producing DNA encoding the modification. Techniques for making insertion, deletion and substitution mutations at predetermined sites in DNA having a known sequence are known. A "modified" protein, nucleic acid or virus is one that has one or more modifications as outlined above.

Monomer: A single molecular unit (such as a protein) that is capable of binding to other molecular units to form dimers or polymers. In the context of the present disclosure, a "TGF-β monomer" is a single TGF-β polypeptide chain, the wild-type version of which can bind other TGF-β monomers to form dimers. In some embodiments herein, the recombinant TGF-β monomers have been engineered to prevent dimerization.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In one example a tumor is a head or neck cancer, such as a squamous cell carcinoma of the head and neck, and can occur in the oral cavity, pharynx, larynx, paranasal sinus and nasal cavity, and salivary glands. In some examples, the head and neck cancer is human papillomavirus positive, such as HPV type 16 positive.

Oncolytic virus: Any virus that preferentially replicates in and kills tumor cells. This term includes naturally occurring oncolytic viruses as well as recombinant viruses designed to target and kill tumor cells. Exemplary oncolytic viruses include, but are not limited to, vaccinia virus, adenovirus, reovirus, herpes simplex virus, measles virus, coxsackievirus, parvovirus, rhinovirus, poliovirus and vesicular stomatitis virus (see, e.g., Raja et al., *J Immunother Cancer* 6: 140, 2018).

Pancreatic cancer: Cancer that begins in the tissues of the pancreas. Pancreatic cancer typically spreads rapidly and is seldom detected at early stages, leading to a poor prognosis for most diagnosed patients. The most common type of pancreatic cancer is pancreatic adenocarcinoma, which accounts for approximately 85% of pancreatic cancer cases.

Peptide or Polypeptide: A polymer in which the monomers are amino acid residues which are joined together through amide bonds. When the amino acids are alpha-amino acids, either the L-optical isomer or the D-optical isomer can be used, the L-isomers being preferred. The terms "peptide," "polypeptide" or "protein" as used herein are intended to encompass any amino acid sequence and include modified sequences, including modified globin proteins. The terms "peptide" and "polypeptide" are specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histidine, is substituted for (or by) an electronegative residue, for example, glutamine or aspartic acid; or (d) a residue having a bulky side chain, for example, phenylalanine, is substituted for (or by) one not having a side chain, for example, glycine.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, PA, 21st Edition (2005), describes compositions and formulations suitable for pharmaceutical delivery of one or more therapeutic compounds, molecules or agents (e.g., oncolytic viruses).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden (such as decrease in the volume or size of a tumor) or a decrease in the number of size of metastases. "Ameliorating" refers to the reduction in the number or severity of signs or symptoms of a disease.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids, proteins and viruses that have been altered by addition, substitution, or deletion of a portion of a natural nucleic acid molecule or protein.

Subject: Living multi-cellular organisms, including vertebrate organisms, a category that includes both human and non-human mammals.

Therapeutically effective amount: A quantity of compound or composition, for instance, an oncolytic virus encoding a recombinant TGF-β monomer, sufficient to achieve a desired effect in a subject being treated. For instance, this can be the amount necessary to inhibit or block TGF-β signaling in a cell. In other instances, this can be the amount necessary to inhibit or suppress growth of a tumor. In one embodiment, a therapeutically effective amount is the amount necessary to eliminate, reduce the size, or prevent metastasis of a tumor, such as reduce a tumor size and/or volume by at least 10%, at least 20%, at least 50%, at least 75%, at least 80%, at least 90%, at least 95%, or even 100%, and/or reduce the number and/or size/volume of metastases by at least 10%, at least 20%, at least 50%, at least 75%, at least 80%, at least 90%, at least 95%, or even 100%, for example as compared to a size/volume/number prior to treatment. In one embodiment, a therapeutically effective amount is the amount necessary to increase the survival time of a subject such as by at least 3 months, at least 4 months, at least 5 months, at least 6 months, at least 9 months, at least 1 year, at least 1.5 years, at least 2 years, at least 3 years, at least 4 years, or at least years, for example as compared to a survival time of a subject with the same cancer without the treatment with the oncolytic virus encoding a recombinant TGF-β monomer. When administered to a subject, a dosage will generally be used that will achieve target tissue concentrations (for example, in tumors) that have been shown to achieve a desired in vitro effect.

Transgene: A gene that has been inserted into the genome of a different organism (such as an oncolytic virus). Transgenes can also be referred to as heterologous genes. In the context of the present disclosure, a transgene can encode, for example, a chemokine, a cytokine, a tumor-associated antigen, an immune co-stimulatory molecule, an immune checkpoint inhibitor, a suicide gene, a tumor suppressor gene, a proapoptotic protein or an anti-angiogenesis protein.

Transforming growth factor-β (TGF-β): A secreted, multifunctional protein that regulates proliferation, cellular differentiation and a number of other cellular functions. Many cells synthesize TGF-β and nearly all cells express receptors for TGF-β. The term "TGF-β" refers to three different protein isoforms, TGF-β1, TGF-β2 and TGF-β3, encoded by the genes TGFB1, TGFB2, TGFB3, respectively.

TGF-β signaling pathway: A signaling pathway involved in a number of cellular processes, such as cell proliferation, differentiation and apoptosis. Members of the TGF-β pathway include, but are not limited to, TGF-β1, TGF-β2, TGF-β3, TGF-β receptor type I and TGF-β receptor type II.

TGF-β receptor: The term "TGF-β receptor" includes TGF-β receptor type I (TβRI, encoded by TGFBR1) and TGF-β receptor type II (TβRII, encoded by TGFBR2). TGF-β receptors are serine/threonine protein kinases. The type I and type II TGF-β receptors form a heterodimeric complex when bound to TGF-β, transducing the TGF-β signal from the cell surface to the cytoplasm.

Vaccinia virus: A large, enveloped virus with a double-stranded DNA genome (~190 kb). Vaccinia virus is a member of the poxvirus family. In some embodiments herein, the vaccinia virus is a Western Reserve strain of vaccinia virus.

III. Overview of Several Embodiments

Immunotherapy has dramatically changed the landscape of cancer treatment (Ribas and Wolchok, *Science* 359(6382):1350-1355, 2018). Most notably, use of monoclonal antibody-mediated blockade of co-inhibitory 'checkpoint' molecules on T cells has resulted in impressive clinical results, FDA approval in multiple indications, and the Nobel Prize in Medicine in 2018. These agents work by reinvigorating tumor-infiltrating T cells, allowing them to differentiate productively and lyse tumor cells. However, success of these agents depends on patients having a dormant, smoldering immune response to cancer cells, including tumor mutational burden (Hellmann et al., *N Engl J Med* 378(22):2093-2104, 2018), pre-existing T cell infiltrate, and high PD-L1 expression. As such, only a minority of patients receive benefit from these therapies. The majority, however, have immunologically 'cold' tumors harboring little or no immune infiltrate. In order to reignite the immune response in these patients, other modalities must be employed to stimulate immune infiltration and antigen release.

Oncolytic viruses represent an attractive means to inflame the tumor microenvironment and stimulate antitumor immunity (Bommareddy et al., *Nat Rev Immunol* 18(8):498-513, 2018; Ribas et al., *Cell* 170(6):1109-1119, 2017). The basic concept behind oncolytic viruses is that by removal of viral genes typically used to promote a proliferative and a transformed-like state, lytic viruses can be engineered to require a transformed cell to replicate (Raja et al., *J Immunother Cancer* 6(1):140, 2018). Genetic engineering strategies can engineer these viruses to selectively infect, replicate in, and immunogenically lyse tumor cells (Raja et al., *J Immunother Cancer* 6(1):140, 2018). Thus, these agents also have the capacity to conscript the strong antiviral immune response as well as vaccinate a patient against their own tumor. More importantly, these viruses, as they selectively replicate in tumor cells, provide the opportunity to deliver genetic cargo to the tumor microenvironment. Indeed, the FDA-approved oncolytic virus T-vec contains a gene encoding GM-CSF to stimulate dendritic cell infiltration and maturation (Ott and Hodi, *Clin Cancer Res* 22(13):3127-3131, 2016). Oncolytic viruses provide immune infiltration, new antitumor immunity, as well as delivery of novel genetically encoded agents to boost therapeutic responses. Thus, oncolytic viruses provide a means for directing tumor cytotoxicity, immunotherapy, and gene therapy of cancer.

The present disclosure describes oncolytic viruses that encode a monomeric form of TGF-β that functions as a dominant negative inhibitor of TGF-β signaling. Provided are oncolytic viruses encoding a recombinant TGF-β monomer having a cysteine to serine substitution, or a cysteine to arginine substitution, at an amino acid residue corresponding to residue 77 of human TGF-β2 set forth as SEQ ID NO: 2; and a deletion of the α3 helix corresponding to amino acid residues 52-71 of human TGF-β2 set forth as SEQ ID NO: 2. These modifications prevent the TGF-β monomers from dimerizing. In some embodiments, the TGF-β monomer is a human, mouse, rat or other mammalian TGF-β monomer. In particular examples, the TGF-β monomer is a human TGF-β monomer.

In some embodiments, the TGF-β monomer is a human TGF-β2 monomer. In some examples, the human TGF-β2 monomer further includes a leucine to arginine substitution at an amino acid residue corresponding to residue 51 of SEQ ID NO: 2; and/or an alanine to lysine substitution at an amino acid residue corresponding to residue 74 of SEQ ID NO: 2. These substitutions increase the net charge of the monomer.

In some embodiments, the human TGF-β2 monomer further includes at least one amino acid substitution that increases affinity of the monomer for MIL In some examples, the at least one amino acid substitution that increases affinity of the monomer for TβRII includes a lysine to arginine substitution at an amino acid residue corresponding to residue 25 of SEQ ID NO: 2; an arginine to lysine substitution at an amino acid residue corresponding to residue 26 of SEQ ID NO: 2; a leucine to valine substitution at an amino acid residue corresponding to residue 89 of SEQ ID NO: 2; an isoleucine to valine substitution at an amino acid residue corresponding to residue 92 of SEQ ID NO: 2; an lysine to arginine substitution at an amino acid residue corresponding to residue 94 of SEQ ID NO: 2; a threonine to lysine substitution at an amino acid residue corresponding to residue 95 of SEQ ID NO: 2; and/or an isoleucine to valine substitution at an amino acid residue corresponding to residue 98 of SEQ ID NO: 2.

In some examples, the human TGF-β2 monomer includes a cysteine to serine substitution at an amino acid residue corresponding to residue 77 of human TGF-β2 set forth as SEQ ID NO: 2; a deletion of the α3 helix corresponding to amino acid residues 52-71 of human TGF-β2 set forth as SEQ ID NO: 2; a lysine to arginine substitution at an amino acid residue corresponding to residue 25 of SEQ ID NO: 2; an arginine to lysine substitution at an amino acid residue corresponding to residue 26 of SEQ ID NO: 2; a leucine to arginine substitution at an amino acid residue corresponding to residue 51 of SEQ ID NO: 2; an alanine to lysine substitution at an amino acid residue corresponding to residue 74 of SEQ ID NO: 2; a leucine to valine substitution at an amino acid residue corresponding to residue 89 of SEQ ID NO: 2; an isoleucine to valine substitution at an amino acid residue corresponding to residue 92 of SEQ ID NO: 2; a lysine to arginine substitution at an amino acid residue corresponding to residue 94 of SEQ ID NO: 2; a threonine to lysine substitution at an amino acid residue corresponding to residue 95 of SEQ ID NO: 2; and an isoleucine to valine substitution at an amino acid residue corresponding to residue 98 of SEQ ID NO: 2.

In particular examples, the amino acid sequence of the human TGF-β2 monomer is at least 95%, at least 96%, at least 97%, at least 98%, or at least 99% identical to SEQ ID NO: 5 or SEQ ID NO: 7. In specific non-limiting examples, the amino acid sequence of the human TGF-β2 monomer comprises or consists of SEQ ID NO: 5 or SEQ ID NO: 7. In some instances, the human TGF-β2 monomer further includes an N-terminal methionine residue.

In some embodiments, the human TGF-β2 monomer includes or further includes at least one amino acid substitution that reduces aggregation and/or improves folding of the monomer. In some examples, the at least one amino acid substitution that reduces aggregation and/or improves folding of the monomer includes a cysteine to valine substitution at an amino acid residue corresponding to residue 7 of SEQ ID NO: 2; a cysteine to alanine substitution at an amino acid residue corresponding to residue 16 of SEQ ID NO: 2; a cysteine to arginine substitution at an amino acid residue corresponding to residue 77 of SEQ ID NO: 2; and/or a valine to arginine substitution at an amino acid residue corresponding to residue 79 of SEQ ID NO: 2.

In particular examples, the human TGF-β2 monomer includes a deletion of the α3 helix corresponding to amino acid residues 52-71 of human TGF-β2 set forth as SEQ ID NO: 2; a lysine to arginine substitution at an amino acid residue corresponding to residue 25 of SEQ ID NO: 2; an arginine to lysine substitution at an amino acid residue corresponding to residue 26 of SEQ ID NO: 2; a leucine to arginine substitution at an amino acid residue corresponding to residue 51 of SEQ ID NO: 2; an alanine to lysine substitution at an amino acid residue corresponding to residue 74 of SEQ ID NO: 2; a cysteine to arginine substitution at an amino acid residue corresponding to residue 77 of SEQ ID NO: 2; a valine to arginine substitution at an amino acid residues corresponding to residue 79 of SEQ ID NO: 2; a leucine to valine substitution at an amino acid residue corresponding to residue 89 of SEQ ID NO: 2; an isoleucine to valine substitution at an amino acid residue corresponding to residue 92 of SEQ ID NO: 2; a lysine to arginine substitution at an amino acid residue corresponding to residue 94 of SEQ ID NO: 2; a threonine to lysine substitution at an amino acid residue corresponding to residue 95 of SEQ ID NO: 2; and an isoleucine to valine substitution at an amino acid residue corresponding to residue 98 of SEQ ID NO: 2. In specific non-limiting examples, the amino acid sequence of the human TGF-β2 monomer comprises or consists of SEQ ID NO: 9. In some instances, the human TGF-β2 monomer further includes an N-terminal methionine residue.

In other particular examples, the human TGF-β2 monomer includes a cysteine to serine substitution at an amino acid residue corresponding to residue 77 of SEQ ID NO: 2; a deletion of the α3 helix corresponding to amino acid residues 52-71 of human TGF-β2 set forth as SEQ ID NO:

2; a cysteine to valine substitution at an amino acid residue corresponding to residue 7 of SEQ ID NO: 2; a cysteine to alanine substitution at an amino acid residue corresponding to residue 16 of SEQ ID NO: 2; a lysine to arginine substitution at an amino acid residue corresponding to residue of SEQ ID NO: 2; a leucine to arginine substitution at an amino acid residue corresponding to residue 51 of SEQ ID NO: 2; an alanine to lysine substitution at an amino acid residue corresponding to residue 74 of SEQ ID NO: 2; and a lysine to arginine substitution at an amino acid residue corresponding to residue 94 of SEQ ID NO: 2. In specific non-limiting examples, the amino acid sequence of the human TGF-β2 monomer comprises or consists of SEQ ID NO: 10. In some instances, the human TGF-β2 monomer further includes an N-terminal methionine residue.

In other particular examples, the human TGF-β2 monomer includes a deletion of the α3 helix corresponding to amino acid residues 52-71 of human TGF-β2 set forth as SEQ ID NO: 2; a cysteine to valine substitution at an amino acid residue corresponding to residue 7 of SEQ ID NO: 2; a cysteine to alanine substitution at an amino acid residue corresponding to residue 16 of SEQ ID NO: 2; a lysine to arginine substitution at an amino acid residue corresponding to residue 25 of SEQ ID NO: 2; an arginine to lysine substitution at an amino acid residue corresponding to residue 26 of SEQ ID NO: 2; a leucine to arginine substitution at an amino acid residue corresponding to residue 51 of SEQ ID NO: 2; an alanine to lysine substitution at an amino acid residue corresponding to residue 74 of SEQ ID NO: 2; a cysteine to arginine substitution at an amino acid residue corresponding to residue 77 of SEQ ID NO: 2; a valine to arginine substitution at an amino acid residues corresponding to residue 79 of SEQ ID NO: 2; a leucine to valine substitution at an amino acid residue corresponding to residue 89 of SEQ ID NO: 2; an isoleucine to valine substitution at an amino acid residue corresponding to residue 92 of SEQ ID NO: 2; a lysine to arginine substitution at an amino acid residue corresponding to residue 94 of SEQ ID NO: 2; a threonine to lysine substitution at an amino acid residue corresponding to residue 95 of SEQ ID NO: 2; and an isoleucine to valine substitution at an amino acid residue corresponding to residue 98 of SEQ ID NO: 2. In specific non-limiting examples, the amino acid sequence of the human TGF-β2 monomer comprises or consists of SEQ ID NO: 12. In some instances, the human TGF-β2 monomer further includes an N-terminal methionine residue.

In alternative embodiments, provided is an oncolytic virus encoding a human recombinant TGF-β2 monomer modified to include the cystine-knot region of PRDC. In some examples, the amino acid sequence of the TGF-β2 monomer is at least 95%, at least 96%, at least 97%, at least 98%, or at least 99% identical to SEQ ID NO: 11. In specific examples, the amino acid sequence of the TGF-β2 monomer comprises or consists of SEQ ID NO: 11. In some instances, the human TGF-β2 monomer further includes an N-terminal methionine residue.

In some embodiments, the TGF-β monomer is a human TGF-β1 monomer. In some examples, the human TGF-β1 monomer further includes an isoleucine to arginine substitution at an amino acid residue corresponding to residue 52 of SEQ ID NO: 1; an alanine to lysine substitution at an amino acid residue corresponding to residue 74 of SEQ ID NO: 1; and/or an alanine to serine substitution at an amino acid residue corresponding to residue 75 of SEQ ID NO: 1. These substitutions increase the net charge of the monomer. In some examples, the human TGF-β1 monomer further includes at least one amino acid substitution that increases affinity of the monomer for TβRII.

In some examples, the amino acid sequence of the human TGF-β1 monomer is at least 95%, at least 96%, at least 97%, at least 98%, or at least 99% identical to SEQ ID NO: 4. In specific non-limiting examples, the amino acid sequence of the human TGF-β1 monomer comprises or consists of SEQ ID NO: 4. In some instances, the human TGF-β1 monomer further includes an N-terminal methionine residue.

In some embodiments, the TGF-β monomer is a human TGF-β3 monomer. In some examples, the human TGF-β3 monomer further includes a leucine to glutamate substitution at an amino acid residue corresponding to residue 51 of SEQ ID NO: 3; an alanine to glutamate substitution at an amino acid residue corresponding to residue 72 of SEQ ID NO: 3; and/or an alanine to aspartate substitution at an amino acid residue corresponding to residue 74 of SEQ ID NO: 3. These substitutions increase the net charge of the monomer. In some examples, the human TGF-β3 monomer further includes at least one amino acid substitution that increases affinity of the monomer for TβRII.

In some examples, the amino acid sequence of the human TGF-β3 monomer is at least 95%, at least 96%, at least 97%, at least 98%, or at least 99% identical to SEQ ID NO: 6. In specific non-limiting examples, the amino acid sequence of the human TGF-β3 monomer comprises or consists of SEQ ID NO: 6. In some instances, the human TGF-β3 monomer further includes an N-terminal methionine residue.

In some embodiments, the TGF-β monomer further comprises a signal sequence, such as a heterologous signal sequence. In some examples, the heterologous signal sequence is an IL-2 signal sequence. In specific examples, the IL-2 signal sequence comprises or consists of the amino acid sequence of SEQ ID NO: 8. In other examples, the heterologous signal sequence is a signal sequence of albumin, trypsinogen-2, immunoglobulin kappa, CD33 or human secreted alkaline phosphatase (SEAP).

The oncolytic virus can be any native or engineered oncolytic virus. In some embodiments, the oncolytic virus is a vaccinia virus, a herpes simplex virus, or an adenovirus. In some examples, the oncolytic virus is a vaccinia virus, such as a Western Reserve strain of vaccinia virus. In particular examples, the oncolytic virus is a vaccinia virus with a modification of the gene encoding thymidine kinase (TK) and a modification of the gene encoding virus growth factor (VGF). For example, the modification can be a complete deletion of the gene, a partial deletion of the gene, an insertion of a heterologous nucleic acid sequence in the gene, or a substitution of a portion of the gene with a heterologous nucleic acid sequence (see, for example, U.S. Pat. No. 7,208,313, which is herein incorporated by reference). In some examples, a nucleic acid sequence encoding the TGF-β monomer is inserted into the gene encoding TK or the gene encoding VGF. In specific examples, the nucleic acid sequence encodes the TGF-β monomer with a signal sequence, such as the IL-2 signal sequence.

Also provided herein are compositions that include an oncolytic virus disclosed herein and a pharmaceutically acceptable carrier, diluent and/or excipient. Also provided herein are tumor cells, such as cancer cells, that include an oncolytic virus disclosed herein, such as a pancreatic cancer cell, melanoma cell, or head and neck cancer cell (such as HNSCC). Further provided are methods of treating cancer in a subject by administering to the subject a therapeutically effective amount of an oncolytic virus or composition disclosed herein. Methods of inhibiting tumor growth or tumor metastasis in a subject with cancer by administering to the subject a therapeutically effective amount of an oncolytic virus or composition disclosed herein are also provided. In some embodiments, the oncolytic virus or composition is administered by subcutaneous, intramuscular, intradermal, intraperitoneal, intravenous, intraprostatic, or intratumoral injection. In some embodiments, the cancer is breast cancer, brain cancer, pancreatic cancer, prostate cancer, skin cancer, bladder cancer, liver cancer, ovarian cancer, renal cancer, endometrial cancer, colorectal cancer, gastric cancer, skin cancer (such as malignant melanoma), head and neck cancer, or thyroid cancer. In specific examples, the cancer is melanoma, head and neck cancer, or pancreatic cancer.

IV. Oncolytic Viruses

Oncolytic viruses are native or modified viruses capable of targeting and killing tumor cells. In many cases, oncolytic viruses designed for immunotherapy are genetically modified to enhance tumor tropism, reduce virulence against normal cells, and/or to express one or more transgenes to promote the anti-tumor response (Raja et al., *J Immunother Cancer* 6:140, 2018; Zheng et al., *Mol Ther Oncolytics* 15:234-247, 2019). For example, oncolytic viruses can be engineered to express cytokines (such as GM-CSF, IFN-α, IFN-β, IFN-γ, IL-2, IL-12, ILK-15, IL-18, IL-21 and IL-24), chemokines (such as CCLS, CCL20, CCL21, DCXCL4L1, and CXCL10), tumor-associated antigens (such as CEA, PSA, hDCT, and CLND6), immune co-stimulatory molecules (for example, CD28, ICOS, OX40, CD30, CD40 and 4-1BB), immune checkpoint inhibitors (such as PD-1, CTLA4, LAG3 and TIM3), suicide genes (for example, HSV-TK, CD, nitroreductase, and cytochrome P450), tumor suppressor genes (such as p53, PTEN, p16, Rb, and MnSOD), proapoptotic proteins (such as apoptin, lactaptin, TRAIL and SMAC) or anti-angiogenesis proteins (VEGI, VEGFR-I-Ig, anti-VEGF antibody, vasculostatin, and FGFR) (for a review, see Zheng et al., *Mol Ther Oncolytics* 15:234-247, 2019; see also U.S. Publication Nos. 2019/0330655 and 2020/0000862, which are herein incorporated by reference). The oncolytic viruses disclosed herein can encode one or more of the above-listed transgenes, or another transgene designed to enhance the anti-tumor response.

The oncolytic viruses disclosed herein can be based on any one of a number of different types of viruses known to be naturally oncolytic or modified to possess oncolytic properties. Oncolytic viruses include, but are not limited to, poxviruses (such as vaccinia virus, cowpox virus, canarypox virus, and fowlpox virus), herpes simplex virus (such as HSV-1), adenovirus, measles virus, reovirus, coxsackievirus, parvovirus, poliovirus, rhinovirus, vesicular stomatitis virus (VSV), mumps virus, Newcastle disease virus (NDV), retroviruses, Seneca Valley virus, or chimeric versions thereof (such as poliovirus/rhinovirus and adenovirus/HSV) (Raja et al., *J Immunother Cancer* 6:140, 2018; Zheng et al., *Mol Ther Oncolytics* 15:234-247, 2019).

In some embodiments herein, the oncolytic virus is a vaccinia virus. The vaccinia virus can be of any strain, such as, for example, Elstree, Wyeth, Copenhagen or Western Reserve. In some examples, the oncolytic vaccinia virus contains one or more genetic modifications, such as mutation or deletion of the gene encoding thymidine kinase (J2R), the genes encoding ribonucleotide reductase (14L and F4L), and/or the gene encoding vaccinia virus growth factor (VGF), each of which play a role in promoting viral replication in normal cells. Other vaccinia virus genes that may be modified include the A56R gene (encoding hemagglutinin), one or more interferon-modulating genes, the B13R gene (encoding a caspase-1 inhibitor), or the F2L gene (encoding viral dUTPase) (see, for example, U.S. Publication Nos. 2019/0330655 and 2020/00197457, which are herein incorporated by reference).

In some embodiments, the oncolytic virus is a Western Reserve strain of vaccinia virus. In particular examples, the Western Reserve strain of vaccinia virus includes a modification of the gene encoding TK and a modification of the gene encoding VGF. For example, the modification can be a complete deletion of the gene, a partial deletion of the gene, an insertion of a heterologous nucleic acid sequence in the gene, or a substitution of a portion of the gene with a heterologous nucleic acid sequence (see, for example, McCart et al., *Cancer Res* 61(24):8751-8757, 2001; and U.S. Pat. No. 7,208,313, which is herein incorporated by reference). In specific non-limiting examples, a nucleic acid sequence encoding the TGF-β monomer with an IL-2 signal sequence is inserted into the gene encoding TK.

V. Pharmaceutical Compositions and Administration of Oncolytic Virus

Provided herein are compositions comprising an oncolytic virus encoding a recombinant TGF-β monomer. The compositions are suitable for formulation and administration in vitro or in vivo. Optionally, the compositions include one or more of the disclosed oncolytic viruses and a pharmaceutically acceptable carrier. Suitable carriers and their formulations are described in *Remington: The Science and Practice of Pharmacy, 22nd Edition*, Loyd V. Allen et al., editors, Pharmaceutical Press (2012). Pharmaceutically acceptable carriers include materials that are not biologically or otherwise undesirable, e.g., the material is administered to a subject without causing undesirable biological effects or interacting in a deleterious manner with the other components of the pharmaceutical composition in which it is contained. If administered to a subject, the carrier is optionally selected to minimize degradation of the active ingredient(s) and to minimize adverse side effects in the subject.

The oncolytic viruses or compositions thereof are administered in accord with known methods, such as by intravenous administration, e.g., as a bolus or by continuous infusion over a period of time. The administration may be local or systemic. The compositions can be administered via any of several routes of administration, including topically, orally, parenterally, intravenously, intra-articularly, intraperitoneally, intramuscularly, intrathecally, subcutaneously, intracavity, transdermally, intrahepatically, intracranially, intracerobrospinal, intrasynovial, intratumoral, nebulization/inhalation, intraprostatic, or by installation via bronchoscopy. Thus, the compositions are administered in a number of ways depending on whether local or systemic treatment is desired, and on the area to be treated.

In some embodiments, the compositions for administration will include an oncolytic virus as described herein in a pharmaceutically acceptable carrier, such as an aqueous carrier. A variety of aqueous carriers can be used, e.g., buffered saline and the like. These solutions are sterile and generally free of undesirable matter. These compositions may be sterilized by conventional sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Pharmaceutical formulations of the oncolytic viruses can be prepared by mixing the oncolytic virus having the desired degree of purity with optional pharmaceutically acceptable carriers, excipients or stabilizers. Such formulations can be lyophilized formulations or aqueous solutions.

Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid), preservatives, low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g., Zn-protein complexes); and/or non-ionic surfactants. The oncolytic virus can be formulated at any appropriate concentration of infectious units or virus particles.

The oncolytic viruses, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the provided methods, compositions can be administered, for example, by intravenous infusion, orally, topically, intraperitoneally, intravesically intratumorally, or intrathecally. In some examples, parenteral administration, intratumoral administration, or intravenous administration are the methods of administration. The formulations of compounds can be presented in unit-dose or multi-dose sealed containers, such as ampules and vials.

Injection solutions and suspensions can be prepared from sterile powders, granules, and tablets of the kind previously described. The pharmaceutical preparation can be in unit dosage form. In such form the preparation is subdivided into unit doses containing appropriate quantities of the active component. Thus, the pharmaceutical compositions can be administered in a variety of unit dosage forms depending upon the method of administration. For example, unit dosage forms suitable for oral administration include, but are not limited to, powder, tablets, pills, capsules and lozenges.

In therapeutic applications, oncolytic viruses or compositions thereof are administered to a subject in an effective amount or dose. Single or multiple administrations of the compositions may be administered as needed. A "patient" or "subject" includes both humans and other animals, particularly mammals. Thus, the methods are applicable to both human therapy and veterinary applications.

An effective amount of an oncolytic virus is determined on an individual basis and is based, at least in part, on the particular oncolytic virus used; the individual's size, age, gender and general health. For example, for administration to a human, at least $10^3$ plaque forming units (PFU) of an oncolytic virus is used, such as at least $10^4$, at least $10^5$, at least $10^6$, at least $10^7$, at least $10^8$, at least $10^9$, at least $10^{10}$, at least $10^{11}$, or at least $10^{12}$ PFU, for example approximately $10^3$ to $10^{12}$ PFU of an oncolytic virus is used, depending on the type, size and number of proliferating cells or neoplasms present. The effective amount can be from about 1.0 pfu/kg body weight to about $10^{15}$ pfu/kg body weight (e.g., from about $10^2$ pfu/kg body weight to about $10^{13}$ pfu/kg body weight). An oncolytic virus is administered in a single dose or in multiple doses (e.g., two, three, four, six, or more doses). Multiple doses can be administered concurrently or consecutively (e.g., over a period of days or weeks).

In some embodiments, the provided methods include administering to the subject one or more therapeutic agents, such as one or more agents for the treatment of cancer, such as breast cancer, brain cancer, pancreatic cancer, prostate cancer, skin cancer, bladder cancer, liver cancer, ovarian cancer, renal cancer, endometrial cancer, colorectal cancer, gastric cancer, skin cancer (such as malignant melanoma), head and neck (e.g., HNSCC), or thyroid cancer.

Administration of the oncolytic viruses can be accompanied by administration of other anti-cancer agents or therapeutic treatments (such as surgical resection of a tumor). Any suitable anti-cancer agent can be administered in combination with the oncolytic viruses disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens), CDK inhibitors and anti-angiogenesis agents. Other anti-cancer treatments include radiation therapy and other antibodies that specifically target cancer cells (e.g., biologics).

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

CDK (Cyclin-dependent kinase) inhibitors are agents that inhibit the function of CDKs. Non-limiting examples of CDK inhibitors for use in the provided methods include AG-024322, AT7519, AZD5438, flavopiridol, indisulam, P1446A-05, PD-0332991, and P276-00 (see e.g., Lapenna et al., *Nature Reviews,* 8:547-566, 2009). Other CDK inhibitors include LY2835219, Palbociclib, LEE011 (Novartis), pan-CDK inhibitor AT7519, seliciclih, CYC065, butyrolactone I, bytnenialdisine, SU9516, CINK4, PD0183812 or fascaplysin.

In some examples, the CDK inhibitor is a broad-range inhibitor (such as flavopiridol, olomoucine, roscovitine, kenpaullone, SNS-032, AT7519, AG-024322, (S)-Roscovitine or R547). In other examples, the CDK inhibitor is a specific inhibitor (such as fascaplysin, ryuvidine, purvalanol A, NU2058, BML-259, SU 9516, PD0332991 or P-276-00).

In one example, the additional therapeutic agent includes one or more immunomodulatory agents, such as, an antagonist of PD-1, an antagonist of PD-L1, a CTLA4 antagonist, or a T cell agonist (such as an agonist of 4-1BB, an agonist of OX40, an agonist of glucocorticoid-induced tumor necrosis factor (TNF) receptor (GITR)), or combinations thereof. In one example, the anti-cancer agent includes a T cell agonist, such as an agonist of 4-1BB, an agonist of OX40, or an agonist of GITR (such as a monoclonal antibody (mAb) specific for an immune check point protein, such as one of the proteins listed above, a ligand of one of these proteins, or an aptamer of one of these proteins). In one example, the additional therapeutic agent includes an antibody that specifically binds and antagonizes PD-1 or PD-L1, such as Atezolizumab, MPDL3280A, BNS-936558 (Nivolumab), Pembrolizumab, Pidilizumab, CT011, AMP-224, AMP-514, MEDI-0680, BMS-936559, BMS935559, MEDI-4736, MPDL-3280A, MSB-0010718C, MGA-271, Indoximod, Epacadostat, BMS-986016, MEDI-4736, MEDI-4737, MK-4166, BMS-663513, PF-05082566 (PF-2566), Lirilumab, or Durvalumab. In one example, the additional therapeutic agent includes an agonist of 4-1BB, such as an antibody, such as PF-05082566 (utomilumab) or BMS-663513 (Urelumab), or a ligand (e.g., 4-1BBL or SA-4-1BBL). In one example, the additional therapeutic agent includes an agonist of OX40, such as a mAb (e.g,. PF-04518600, MEDI6469, MEDI0562, MEDI6383, MOXR0916, BMS 986178, or GSK3174998), or a ligand (e.g., OX40L). In one example, the additional therapeutic agent includes an agonist GITR, such as a mAb, such as DTA-1, TRX518, MK-4166, MK-1248, AMG 228, INCAGN01876, GWN323 (from Novartis), CK-302 (from Checkpoint Therapeutics) or BMS-986156. In one example, the additional therapeutic agent includes an agonists of GITR, such as a GITR ligand (GITRL), such as a natural GITRL or a multivalent GITR ligand fusion protein, such as MEDI1873. In one example, the additional therapeutic agent includes anti-CTLA4 (e.g., ipilimumab). In one example, the additional therapeutic agent includes anti-EGFR (e.g., cetuximab), anti-VEGF (e.g., bevacizumab), alemtuzumab, gemtuzumab, rituximab, panitumumab, pertuzumab, trastuzumab, and/or other therapeutic monoclonal antibody.

The choice of agent and dosage can be determined based on the given disease being treated. Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions.

VI. Exemplary Embodiments

Embodiment 1. An oncolytic virus encoding a human recombinant transforming growth factor (TGF)-β2 monomer, comprising:

a cysteine to serine or a cysteine to arginine substitution at an amino acid residue corresponding to residue 77 of human TGF-β2 set forth as SEQ ID NO: 2;

a deletion of the α3 helix corresponding to amino acid residues 52-71 of human TGF-β2 set forth as SEQ ID NO: 2;

a lysine to arginine substitution at an amino acid residue corresponding to residue 25 of SEQ ID NO: 2;

an arginine to lysine substitution at an amino acid residue corresponding to residue 26 of SEQ ID NO: 2;

a leucine to arginine substitution at an amino acid residue corresponding to residue 51 of SEQ ID NO: 2;

an alanine to lysine substitution at an amino acid residue corresponding to residue 74 of SEQ ID NO: 2;

a leucine to valine substitution at an amino acid residue corresponding to residue 89 of SEQ ID NO: 2;

an isoleucine to valine substitution at an amino acid residue corresponding to residue 92 of SEQ ID NO: 2;

a lysine to arginine substitution at an amino acid residue corresponding to residue 94 of SEQ ID NO: 2;

a threonine to lysine substitution at an amino acid residue corresponding to residue 95 of SEQ ID NO: 2; and an isoleucine to valine substitution at an amino acid residue corresponding to residue 98 of SEQ ID NO: 2.

Embodiment 2. An oncolytic virus encoding a human recombinant transforming growth factor (TGF)-β monomer, comprising:

a leucine to arginine substitution at an amino acid residue corresponding to residue 51 of SEQ ID NO: 2;

an alanine to lysine substitution at an amino acid residue corresponding to residue 74 of SEQ ID NO: 2;

a cysteine to serine or a cysteine to arginine substitution at an amino acid residue corresponding to residue 77 of human TGF-β2 set forth as SEQ ID NO: 2; and a deletion of the α3 helix corresponding to amino acid residues 52-71 of human TGF-β2 set forth as SEQ ID NO: 2.

Embodiment 3. The oncolytic virus of embodiment 2, wherein the TGF-β monomer is a human TGF-β2 monomer.

Embodiment 4. The oncolytic virus of embodiment 3, wherein the human TGF-β2 monomer further comprises at least one amino acid substitution that increases affinity of the monomer for TGF-β receptor II (TβRII).

Embodiment 5. The oncolytic virus of embodiment 4, wherein the at least one amino acid substitution that increases affinity of the monomer for TβRII comprises:

a lysine to arginine substitution at an amino acid residue corresponding to residue 25 of SEQ ID NO: 2;

an arginine to lysine substitution at an amino acid residue corresponding to residue 26 of SEQ ID NO: 2;

a leucine to valine substitution at an amino acid residue corresponding to residue 89 of SEQ ID NO: 2;

an isoleucine to valine substitution at an amino acid residue corresponding to residue 92 of SEQ ID NO: 2;

a lysine to arginine substitution at an amino acid residue corresponding to residue 94 of SEQ ID NO: 2;

a threonine to lysine substitution at an amino acid residue corresponding to residue 95 of SEQ ID NO: 2; and/or an isoleucine to valine substitution at an amino acid residue corresponding to residue 98 of SEQ ID NO: 2.

Embodiment 6. The oncolytic virus of any one of embodiments 1-5, wherein the human TGF-β2 monomer comprises:

a cysteine to serine substitution at an amino acid residue corresponding to residue 77 of human TGF-β2 set forth as SEQ ID NO: 2;

a deletion of the c 3 helix corresponding to amino acid residues 52-71 of human TGF-β2 set forth as SEQ ID NO: 2;

a lysine to arginine substitution at an amino acid residue corresponding to residue 25 of SEQ ID NO: 2;

an arginine to lysine substitution at an amino acid residue corresponding to residue 26 of SEQ ID NO: 2;

a leucine to arginine substitution at an amino acid residue corresponding to residue 51 of SEQ ID NO: 2;

an alanine to lysine substitution at an amino acid residue corresponding to residue 74 of SEQ ID NO: 2;

a leucine to valine substitution at an amino acid residue corresponding to residue 89 of SEQ ID NO: 2;

an isoleucine to valine substitution at an amino acid residue corresponding to residue 92 of SEQ ID NO: 2;

a lysine to arginine substitution at an amino acid residue corresponding to residue 94 of SEQ ID NO: 2;

a threonine to lysine substitution at an amino acid residue corresponding to residue 95 of SEQ ID NO: 2; and an isoleucine to valine substitution at an amino acid residue corresponding to residue 98 of SEQ ID NO: 2.

Embodiment 7. The oncolytic virus of any one of embodiments 1-6, wherein the amino acid sequence of the human TGF-β2 monomer comprises or consists of SEQ ID NO: 7.

Embodiment 8. The oncolytic virus of any one of embodiments 1-5, wherein the human TGF-β2 monomer comprises or further comprises at least one amino acid substitution that reduces aggregation and/or improves folding of the monomer.

Embodiment 9. The oncolytic virus of embodiment 8, wherein the human TGF-β2 monomer comprises:

a cysteine to valine substitution at an amino acid residue corresponding to residue 7 of SEQ ID NO: 2;

a cysteine to alanine substitution at an amino acid residue corresponding to residue 16 of SEQ ID NO: 2;

a cysteine to arginine substitution at an amino acid residue corresponding to residue 77 of SEQ ID NO: 2; and/or a valine to arginine substitution at an amino acid residue corresponding to residue 79 of SEQ ID NO: 2.

Embodiment 10. The oncolytic virus of embodiment 9, wherein the human TGF-β2 monomer comprises:

a deletion of the α3 helix corresponding to amino acid residues 52-71 of human TGF-β2 set forth as SEQ ID NO: 2;

a lysine to arginine substitution at an amino acid residue corresponding to residue 25 of SEQ ID NO: 2;

an arginine to lysine substitution at an amino acid residue corresponding to residue 26 of SEQ ID NO: 2;

a leucine to arginine substitution at an amino acid residue corresponding to residue 51 of SEQ ID NO: 2;

an alanine to lysine substitution at an amino acid residue corresponding to residue 74 of SEQ ID NO: 2;

a cysteine to arginine substitution at an amino acid residue corresponding to residue 77 of SEQ ID NO: 2;

a valine to arginine substitution at an amino acid residues corresponding to residue 79 of SEQ ID NO: 2;

a leucine to valine substitution at an amino acid residue corresponding to residue 89 of SEQ ID NO: 2;

an isoleucine to valine substitution at an amino acid residue corresponding to residue 92 of SEQ ID NO: 2;

a lysine to arginine substitution at an amino acid residue corresponding to residue 94 of SEQ ID NO: 2;

a threonine to lysine substitution at an amino acid residue corresponding to residue 95 of SEQ ID NO: 2; and an isoleucine to valine substitution at an amino acid residue corresponding to residue 98 of SEQ ID NO: 2.

Embodiment 11. The oncolytic virus of embodiment 10, wherein the amino acid sequence of the human TGF-β2 monomer comprises or consists of SEQ ID NO: 9.

Embodiment 12. The oncolytic virus of embodiment 9, wherein the human TGF-β2 monomer comprises:

a cysteine to serine substitution at an amino acid residue corresponding to residue 77 of SEQ ID NO: 2;

a deletion of the α3 helix corresponding to amino acid residues 52-71 of human TGF-β2 set forth as SEQ ID NO: 2;

a cysteine to valine substitution at an amino acid residue corresponding to residue 7 of SEQ ID NO: 2;

a cysteine to alanine substitution at an amino acid residue corresponding to residue 16 of SEQ ID NO: 2;

a lysine to arginine substitution at an amino acid residue corresponding to residue 25 of SEQ ID NO: 2;

a leucine to arginine substitution at an amino acid residue corresponding to residue 51 of SEQ ID NO: 2;

an alanine to lysine substitution at an amino acid residue corresponding to residue 74 of SEQ ID NO: 2; and a lysine to arginine substitution at an amino acid residue corresponding to residue 94 of SEQ ID NO: 2.

Embodiment 13. The oncolytic virus of embodiment 12, wherein the amino acid sequence of the human TGF-β2 monomer comprises or consists of SEQ ID NO: 10.

Embodiment 14. The oncolytic virus of embodiment 9, wherein the human TGF-β2 monomer comprises:

a deletion of the α3 helix corresponding to amino acid residues 52-71 of human TGF-β2 set forth as SEQ ID NO: 2;

a cysteine to valine substitution at an amino acid residue corresponding to residue 7 of SEQ ID NO: 2;

a cysteine to alanine substitution at an amino acid residue corresponding to residue 16 of SEQ ID NO: 2;

a lysine to arginine substitution at an amino acid residue corresponding to residue 25 of SEQ ID NO: 2;

an arginine to lysine substitution at an amino acid residue corresponding to residue 26 of SEQ ID NO: 2;

a leucine to arginine substitution at an amino acid residue corresponding to residue 51 of SEQ ID NO: 2;

an alanine to lysine substitution at an amino acid residue corresponding to residue 74 of SEQ ID NO: 2;

a cysteine to arginine substitution at an amino acid residue corresponding to residue 77 of SEQ ID NO: 2;

a valine to arginine substitution at an amino acid residues corresponding to residue 79 of SEQ ID NO: 2;

a leucine to valine substitution at an amino acid residue corresponding to residue 89 of SEQ ID NO: 2;

an isoleucine to valine substitution at an amino acid residue corresponding to residue 92 of SEQ ID NO: 2;

a lysine to arginine substitution at an amino acid residue corresponding to residue 94 of SEQ ID NO: 2;

a threonine to lysine substitution at an amino acid residue corresponding to residue 95 of SEQ ID NO: 2; and an isoleucine to valine substitution at an amino acid residue corresponding to residue 98 of SEQ ID NO: 2.

Embodiment 15. The oncolytic virus of embodiment 13, wherein the amino acid sequence of the human TGF-β2 monomer comprises or consists of SEQ ID NO: 12.

Embodiment 16. An oncolytic virus encoding a human recombinant transforming growth factor (TGF)-132 monomer, wherein the amino acid sequence of the TGF-β2 monomer comprises or consists of SEQ ID NO: 11.

Embodiment 17. The oncolytic virus of embodiment 1, wherein the TGF-β monomer is a human TGF-β1 monomer.

Embodiment 18. The oncolytic virus of embodiment 17, wherein the human TGF-β1 monomer further comprises:

an isoleucine to arginine substitution at an amino acid residue corresponding to residue 52 of SEQ ID NO: 1;

an alanine to lysine substitution at an amino acid residue corresponding to residue 74 of SEQ ID NO: 1;

an alanine to serine substitution at an amino acid residue corresponding to residue 75 of SEQ ID NO: 1; or an isoleucine to arginine substitution at an amino acid residue corresponding to residue 52, an alanine to lysine substitution at an amino acid residue corresponding to residue 74 and an alanine to serine substitution at an amino acid residue corresponding to residue 75 of SEQ ID NO: 1.

Embodiment 19. The oncolytic virus of embodiment 17 or embodiment 18, wherein the amino acid sequence of the human TGF-β1 monomer comprises or consists of SEQ ID NO: 4.

Embodiment 20. The oncolytic virus of embodiment 2, wherein the TGF-β monomer is a human TGF-β3 monomer.

Embodiment 21. The oncolytic virus of embodiment 20, wherein the human TGF-β3 monomer further comprises:

a leucine to glutamate substitution at an amino acid residue corresponding to residue 51 of SEQ ID NO: 3;

an alanine to glutamate substitution at an amino acid residue corresponding to residue 72 of SEQ ID NO: 3;

an alanine to aspartate substitution at an amino acid residue corresponding to residue 74 of SEQ ID NO: 3; or a leucine to glutamate substitution at an amino acid residue corresponding to residue 51, an alanine to glutamate substitution at an amino acid residue corresponding to residue 72 and an alanine to aspartate substitution at an amino acid residue corresponding to residue 74 of SEQ ID NO: 3.

Embodiment 22. The oncolytic virus of embodiment 20 or embodiment 21, wherein the amino acid sequence of the human TGF-β3 monomer comprises or consists of SEQ ID NO: 6.

Embodiment 23. The oncolytic virus of any one of embodiments 1-22, wherein the TGF-β monomer further comprises a signal sequence.

Embodiment 24. The oncolytic virus of embodiment 23, wherein the signal sequence is an IL-2 signal sequence comprising the amino acid sequence of SEQ ID NO: 8.

Embodiment 25. The oncolytic virus of any one of embodiments 1-24, wherein the virus is a vaccinia virus, a herpes simplex virus, or an adenovirus.

Embodiment 26. The oncolytic virus of any one of embodiments 1-25, wherein the virus is a vaccinia virus.

Embodiment 27. The oncolytic virus of embodiment 26, wherein the vaccinia virus comprises a modification of the gene encoding thymidine kinase (TK) and a modification of the gene encoding virus growth factor (VGF).

Embodiment 28. The oncolytic virus of embodiment 27, wherein the modification of the gene encoding TK comprises a complete or partial deletion of the gene.

Embodiment 29. The oncolytic virus of embodiment 27 or embodiment 28, wherein at least a portion of the TK gene is replaced with a nucleic acid encoding the TGF-β monomer.

Embodiment 30. The oncolytic virus of any one of embodiments 27-29, wherein the modification of the gene encoding VGF comprises a complete or partial deletion of the gene.

Embodiment 31. A composition comprising the oncolytic virus of any one of embodiments 1-30 and a pharmaceutically acceptable carrier.

Embodiment 32. A method of treating cancer in a subject, comprising administering to the subject a therapeutically effective amount of the oncolytic virus of any one of embodiments 1-30 or the composition of embodiment 31.

Embodiment 33. A method of inhibiting tumor growth or tumor metastasis in a subject with cancer, comprising administering to the subject a therapeutically effective amount of the oncolytic virus of any one of embodiments 1-30 or the composition of embodiment 31.

Embodiment 34. The method of embodiment 32 or embodiment 33, wherein the cancer is melanoma, head and neck cancer, or pancreatic cancer.

The following examples are provided to illustrate certain particular features and/or embodiments. These examples should not be construed to limit the disclosure to the particular features or embodiments described.

EXAMPLES

Example 1

Recombinant TGF-β Mini-Monomers

Recombinant forms of human TGF-β that are unable to dimerize were designed as described in WO 2018/094173 (herein incorporated by reference in its entirety). Specifically, recombinant forms of human TGF-β1, human TGF-β2, and human TGF-β3 having a deletion of the α-helix 3 and several flanking residues (corresponding to residues 52-71 of each protein) and a cysteine to serine substitution at residue 77 were generated. The length of the deletion was chosen in order to leave a sufficient number of residues between the last residue of β-strand 4 (Gly-48) and the first residue of β-strand 5 (Cys-77/Ser-77) to form an unconstrained loop that bridges β-strands 4 and 5. Additionally, either two (TGF-β2) or three (TGF-β1 and -β3) of the loop-forming residues were substituted to increase the net overall charge at pH 7.0 for the full-length TGF-β1, -(β2, and −β3 monomers from −0.9, +1.1, and +4.4 to −3.1, +3.9, and +6.1, respectively. TGF-β proteins having these modifications are referred to herein as "mini-monomers" and are designated as mmTGF-β1, mmTGF-β2, and mmTGF-β3. An additional TGF-β2 mini-monomer having seven amino acid substitutions that increase its affinity for the TGF-β type II receptor (TβRII) was designed; this mini-monomer is referred to herein as "mmTGF-β2-7M" or "dnTGFβ2$^{mm}$." Descriptions of the wild-type TGF-β and variant TGF-β mini-monomers disclosed herein are provided in Table 1. Sequences of the proteins are set forth as SEQ ID NOs: 1-7 (and shown below). Positions of the single amino acid substitutions and deletions are relative to the corresponding wild-type TGF-β protein.

TABLE 1

| TGF-β variants | | | | | |
|---|---|---|---|---|---|
| Variant Name | SEQ ID NO | Description | Length of monomer | Single amino acid substitutions | Deletion |
| TGF-β1 | 1 | Human TGF-β1 wild type homodimer | 112 a.a. | None | None |
| TGF-β2 | 2 | Human TGF-β2 wild type homodimer | 112 a.a. | None | None |
| TGF-β3 | 3 | Human TGF-β3 wild type homodimer | 112 a.a. | None | None |
| mmTGF-β1 | 4 | Human TGF-β1 mini-monomer | 92 a.a. | I52R, A74K, A75S, C77S | Residues 52-71 |
| mmTGF-β2 | 5 | Human TGF-β2 mini-monomer | 92 a.a. | L51R, A74K, C77S | Residues 52-71 |
| mmTGF-β3 | 6 | Human TGF-β3 mini-monomer | 92 a.a. | L51E, A72E, A74D, C77S | Residues 52-71 |
| mmTGF-β2-7M | 7 | Human TGF-β2 mini-monomer with increased affinity for TβRII | 92 a.a. | K25R, R26K, L51R, A74K, C77S, L89V, I92V, K94R, T95K, I98V | Residues 52-71 |

TGF-β1

SEQ ID NO: 1

```
ALDTNYCFSSTEKNCCVRQLYIDFRKDLGWKWIHE
PKGYHANFCLGPCPYIWSLDTQYSKVLALYNQHNP
GASAAPCCVPQALEPLPIVYYVGRKPKVEQLSNMI
VRSCKCS
```

TGF-β2

SEQ ID NO: 2

```
ALDAAYCFRNVQDNCCLRPLYIDFKRDLGWKWIHE
PKGYNANFCAGACPYLWSSDTQHSKVLSLYNTINP
EASASPCCVSQDLEPLTILYYIGKTPKIEQLSNMI
VKSCKCS
```

TGF-β3

SEQ ID NO: 3

```
ALDTNYCFRNLEENCCVRPLYIDFRQDLGWKWVHE
PKGYYANFCSGPCPYLRSADTTHSTVLGLYNTLNP
EASASPCCVPQDLEPLTILYYVGRTPKVEQLSNMV
VKSCKCS
```

-continued mmTGF-β1

SEQ ID NO: 4

```
ALDTNYCFSSTEKNCCVRQLYIDFRKDLGWKWIHE
PKGYHANFCLGPCPYRASKSPSCVPQALEPLPIVY
YVGRKPKVEQLSNMIVRSCKCS
```

mmTGF-β2

SEQ ID NO: 5

```
ALDAAYCFRNVQDNCCLRPLYIDFKRDLGWKWIHE
PKGYNANFCAGACPYRASKSPSCVSQDLEPLTIL
YYIGKTPKIEQLSNMIVKSCKCS
```

-continued mmTGF-β3

SEQ ID NO: 6

```
ALDTNYCFRNLEENCCVRPLYIDFRQDLGWKWVHE
PKGYYANFCSGPCPYEESDSPSCVPQDLEPLTILY
YVGRTPKVEQLSNMVVKSCKCS
```

mmTGF-β2-7M

SEQ ID NO: 7

```
ALDAAYCFRNVQDNCCLRPLYIDFRKDLGWKWIHE
PKGYNANFCAGACPYRASKSPSCVSQDLEPLTIVY
YVGRKPKVEQLSNMIVKSCKCS
```

In some embodiments, any of the above sequences include an N-terminal methionine (M) residue.

In some embodiments herein, the TGF-β monomer includes an N-terminal signal sequence, such as the IL-2 signal sequence MYRMQLLSCIALSLALVTNS (SEQ ID NO: 8).

Example 2

Metabolic Modulation of the Tumor Microenvironment Using Oncolytic Viruses

Immunity faces many barriers within the tumor microenvironment, and central among these is a tumor's distinct metabolic landscape (Scharping and Delgoffe, *Vaccines* (Basel) 4(4):46, 2016). As cancer cells proliferate, they deplete the local environment of nutrients and oxygen while causing the buildup of toxic byproducts like lactic acid. Thus, infiltrating immune cells must endure both immune and metabolic suppression within the tumor microenvironment (Najjar et al., *JCI Insight* 4(5):e124989, 2019). It is believed that metabolic support is crucial for curative immunotherapy for cancer. T cells infiltrating tumors do so at a severe metabolic disadvantage, repressing their ability to take up glucose and losing functional mitochondrial mass (Scharping et al., *Immunity* 45(2):374-388, 2016). In addition, several immunotherapeutic modalities can be improved through metabolic means, including mitochondrial reprogramming of adoptive cell therapies (Scharping et al., *Immunity* 45(2):374-388, 2016) and pharmacologic (Scharping et al., *Cancer Immunol Res* 5(1):9-16, 2016) and immunotherapeutic (Menk et al., *J Exp Med* 215(4):1091-1100, 2018) metabolic enhancement of checkpoint blockade. Oncolytic virus immunotherapy can be improved by genetically encoding a metabolic modulator rather than an immune stimulator (such as GM-CSF). The gene encoding the adipokine leptin was inserted into oncolytic vaccinia virus, enforcing leptin expression specifically in the tumor microenvironment (Rivadeneira et al., *Immunity* 51(3):548-560, 2019). As tumor infiltrating T cells express high levels of the leptin receptor, they receive a metabolic reprogramming signal upon treatment with this virus. Indeed, it was found that leptin acted on new tumor infiltrating T cells, enhancing mitochondrial activity and promoting robust antitumor immunity and long-term memory in murine models of melanoma and pancreatic cancer. Further, in the course of these studies, the first complete characterization of the immune infiltrate induced by oncolytic viruses was delineated by scRNA-seq. These studies revealed that while oncolytic viruses induce a robust remodeling of the immunologic environment in cancer, these new T cell immigrants still experience immunologic repression via TGF-β signaling and metabolic repression through exposure to hypoxia and continuous antigen stimulation.

The examples disclosed herein describe how oncolytic viruses can be used to deliver metabolic modulation to the tumor microenvironment. As oncolytic viruses 'transduce' the tumor cells they infect, the agent itself can be used to deliver gene therapy to the tumor. An oncolytic version of the Western Reserve strain of Vaccinia virus (lacking thymidine kinase and viral growth factor genes) (McCart et al., *Cancer Res* 61(24):8751-8757, 2001) was used for these studies. Vaccinia virus is an effective oncolytic because it encodes its own polymerase and replicates in the cytoplasm, it replicates well in hypoxic conditions, and its large genome means it can be deeply engineered to express multiple transgenes (Yang et al., *J Cancer Res Clin Oncol* 144(12):2433-2440, 2018).

scRNAseq was used to ascertain the immediate consequences of oncolytic virus infection (Rivadeneira et al., *Immunity* 51(3):548-560, 2019). Specifically, the CD45+ infiltrate was profiled 7 days after infection with oncolytic VV (oVV) or a PBS control (FIGS. 1A and 1B). This analysis revealed a striking remodeling of the tumor microenvironment, with the CD45+ infiltrate being dominated by new, effector/memory T cells that were clonally distinct (FIG. 1C and Rivadeneira et al., *Immunity* 51(3):548-560, 2019). However, that new infiltrate was ultimately ineffective, as tumors treated with this virus eventually evaded and grew unrestrained. Thus, while oVV can inflame the tumor and promote new infiltrate, there are other inhibitory mechanisms at play. Deeper analysis of the 7-day infiltrate revealed that while those T cells were effector/memory-like, they also contained a transcriptomic signature consistent with TGF-β signaling (FIG. 1D). Further, metabolic analysis revealed these T cells still succumbed to metabolic insufficiency (FIG. 1E) (Rivadeneira et al., *Immunity* 51(3):548-560, 2019).

Thus, while oncolytic viruses can stimulate tumor inflammation and T cell infiltration, that new infiltrate, mainly T cell-driven, experiences metabolic and immunologic barriers that prevent complete responses. In the examples below, oncolytic virus is used to express genetic constructs that act to temper these barriers.

Example 3

Engineered Targeting of TGF-β Signaling within the Tumor Microenvironment Using Oncolytic Viral Delivery of a Novel TGF-β Inhibitor TGF-β represents a potent immunosuppressive signal within cancer, and acts through multiple pathways to inhibit antitumor immunity (Ungefroren, *Expert Opin Ther Targets* 23(8):679-693, 2019; Derynck and Budi, *Sci Signal* 12(570):eaav5183, 2019). As the signatures of TGF-β signaling were highly evident even in oVV-induced infiltrate, steps were taken to generate agents that could target the suppressive environment enforced by TGF-β. However, despite its attractive profile as a target, safe and effective TGF-β inhibitors have remained elusive (Connolly et al., *Int J Biol Sci* 8(7):964-978, 2012; Akhurst, *Cold Spring Harb Perspect Biol* 9(10):a022301, 2017). As a pleiotropic cytokine, inhibiting its activity systemically is not without risk, and kinase inhibitors aimed at targeting the activity of the receptor have severe off-target effects (Connolly et al., *Int J Biol Sci* 8(7):964-978, 2012; Akhurst, *Cold Spring Harb Perspect Biol* 9(10):a022301, 2017). It was reasoned that a potent genetically encoded inhibitor might be well tolerated if encoded in an oncolytic virus, as the agent would only be expressed by infected tumor cells and thus limited to the tumor microenvironment.

With this goal in mind, the antitumor activity of a genetically encoded TGF-β inhibitor (Kim et al., *J Biol Chem* 292(17):7173-7188, 2017) was evaluated. This inhibitor is an engineered TGF-β2 molecule that lacks a cysteine critical for disulfide bond-mediated dimerization (and thus exists as a monomer), but also replaces a 'heel' helix with an inverted loop, preventing recruitment of TGF-β receptor I (TβRI) (see Example 1). Thus, this 'mini-monomer' monogamously and potently binds TGF-β receptor II (TβRII) as a monomer and prevents recruitment of TORI. In this way, it acts as a dominant negative (FIG. 2A) (Kim et al., *J Biol Chem* 292(17):7173-7188, 2017). Indeed, the mini-monomer binds the receptor with heightened affinity and has no signaling activity of its own (FIG. 2B). Additionally, it potently inhibits TGF-β1, TGF-β2 and TGF-β3 signaling in a reporter cell line (FIG. 2B). The engineered construct, with an IL-2 signal peptide (SEQ ID NO: 8), was cloned into the TK locus of oncolytic vaccinia virus. Viral infection of tumor cells induced expression of the mini-monomeric TGF-β (FIG. 3A), and supernatants from those tumor cells suppressed TGF-β signaling (FIG. 3B). When used as a therapy in B16 melanoma, VV-dnTgfb2$^{mm}$ induced a more potent antitumor response (FIG. 3C).

Example 4

Immunologic and Environmental Consequences of Oncolytic Virus Encoded TFG-β Inhibition (VV-dnTgfb2$^{mm}$)

As a pleiotropic cytokine, targeting TGF-β may act on many players within the tumor microenvironment (Derynck and Budi, *Sci Signal* 12(570):eaav5183, 2019). Thus, to understand the immunologic consequences of virus-delivered TGF-β inhibition, several orthogonal approaches are employed. For these studies, both melanoma and pancreatic cancer cell lines are used as models of immunologically active versus inactive tumors. Mice bearing B16 or clone24 (a cell line generated from a melanoma generated in a Pten/Braf mouse model; Najjar et al., *JCI Insight* 4(5): e124989, 2019) melanoma, or Panc02 pancreatic tumors, receive an intratumoral injection of 2.5×10 6 PFU of either control oncolytic or virus expressing dnTGFβ2$^{mm}$.

The 'geography' of the tumor microenvironment is interrogated using a highly multiplexed imaging technique (co-detection by indexing, or CODEX), which utilizes oligo-tagged antibodies and base-additive imaging to iteratively image dozens of antibodies on a single section (Goltsev et al., *Cell* 174(4):968-981, 2018). This technology is used to examine the location and status of multiple immune and stromal subsets. Using anti-vaccinia and anti-phosphoSmad3 antibodies enables identification of infected cells and also assessment of the impact on TGF-β signaling in situ.

scRNAseq is used to determine the cellular and transcriptional changes induced by this viral manipulation. Whole tumor homogenates or CD45+ enriched fractions are used, and compared to the control oncolytic as well as control injections using a 10× Genomics Chromium controller (Rivadeneira et al., *Immunity* 51(3):548-560, 2019).

1

These observations are confirmed and further interrogated using highly multiplexed flow cytometry to immunologically profile and functionally assess the quality of the tumor infiltrate after VV-dnTgfb2$^{mm}$ therapy.

Example 5

Therapeutic Consequences of VV-dnTgfb2" in Clone24 and Panc02 Models

The therapeutic efficacy of a TGF-β targeting oncolytic virus is tested in injectable models of melanoma (clone24) and pancreatic cancer (Panc02), which respond partially to oVV but more completely to immunologically/metabolically engineered strains (Rivadeneira et al., *Immunity* 51(3): 548-560, 2019). Mice bearing 3-4 mm tumors receive a single intratumoral injection of $2.5\times10^{6}$ PFU of either VV-dnTgfb2$^{mm}$ or a control oncolytic virus. Tumor growth is tracked using digital calipers and survival is calculated based on IACUC guidelines for sacrifice (tumors reaching 15 mm in any direction).

In mice that experience complete responses, survivors are kept for 3-4 weeks and then re-injected with the parental tumor (no virus treatment). At the same time, a second cohort of naïve mice is injected with the parental tumor. If mice carry immunologic memory to the tumor, they reject the tumor or resist tumor growth relative to the naïve mouse cohort.

Additional experiments employ multiple viral injections, and tumor models in which mice bear two identical tumors, but only one is injected with virus.

Example 6

Additional Modifications of TGF-β2 Monomers for In Vivo Administration

This example describes studies to evaluate modifications to enhance in vivo delivery of TGF-β monomers. Four variants of mmTGF-β2-7M were generated, which are described in Table 2. The positions of the single amino acid substitutions and deletions are relative to human TGF-β2 set forth as SEQ ID NO: 2.

TABLE 2

Additional TGF-β mini-monomer variants

| Variant Name | SEQ ID NO | Variant Description | Length of monomer | Single amino acid substitutions | Deletion |
|---|---|---|---|---|---|
| mmTGF-β2-7M2R | 9 | Human TGF-β2 mini-monomer with increased affinity for TBRII and reduced aggregation | 92 a.a. | K25R, R26K, L51R, A74K, C77R, V79R, L89V, I92V, K94R, T95K, I98V | Residues 52-71 |
| mmTGF-β2-2M-Del8-17 | 10 | Human TGF-β2 mini-monomer with increased affinity for TBRII and improved folding | 92 a.a. | C7V, C16A, K25R, L51R, A74K, C77S, K94R | Residues 52-71 |
| mmTGF-β2-7M-PRDC | 11 | Human TGF-β2 mini-monomer including Finger 1-2 and Finger 3-4 grafted with cystine knot region of PRDC | 115 a.a. | K25R, R26K, L89V, I92V, K94R, T95K, I98V | See FIG. 4D |
| mmTGF-β2-7M2R-Del8-17 (also referred to as "var1") | 12 | Human TGF-β2 mini-monomer with increased affinity for TBRII, reduced aggregation and improved folding | 92 a.a. | C7V, C16A, K25R, R26K, L51R, A74K, C77R, V79R, L89V, I92V, K94R, T95K, I98V | Residues 52-71 |

mmTGF-β2-7M2R

SEQ ID NO: 9

```
ALDAAYCFRNVQDNCCLRPLYIDFRKDLGWKWIHE

PKGYNANFCAGACPYRASKSPRCRSQDLEPLTIVY

YVGRKPKVEQLSNMIVKSCKCS
```

mmTGF-β2-2M-Del8-17

SEQ ID NO: 10

```
ALDAAYVFRNVQDNCALRPLYIDFRRDLGWKWIHE

PKGYNANFCAGACPYRASKSPSCVSQDLEPLTIL

YYIGRTPKIEQLSNMIVKSCKCS
```

mmTGF-β2-7M-PRDC

SEQ ID NO: 11

```
KEVLASSQEALVVTERKYLKSDWCKLRPLYIDFRK

DLGWKWIHEPKGYNANFCYGQCNSFYIPRHVKKEE

DSFQSSAFCVSQDLEPLTIVYYVGRKPKVEQLSNM

IVKSCRCMSV
```

mmTGF-β2-7M2R-Del8-17

SEQ ID NO: 12

```
ALDAAYVFRNVQDNCALRPLYIDFRKDLGWKWIHE

PKGYNANFCAGACPYRASKSPRCRSQDLEPLTIVY

YVGRKPKVEQLSNMIVKSCKCS
```

In some embodiments, any of the above sequences include an N-terminal methionine (M) residue.

Elimination or Reduction in the Propensity to Aggregate

Figures 5A, 5B, 5C, 5D, 5E, 5F:
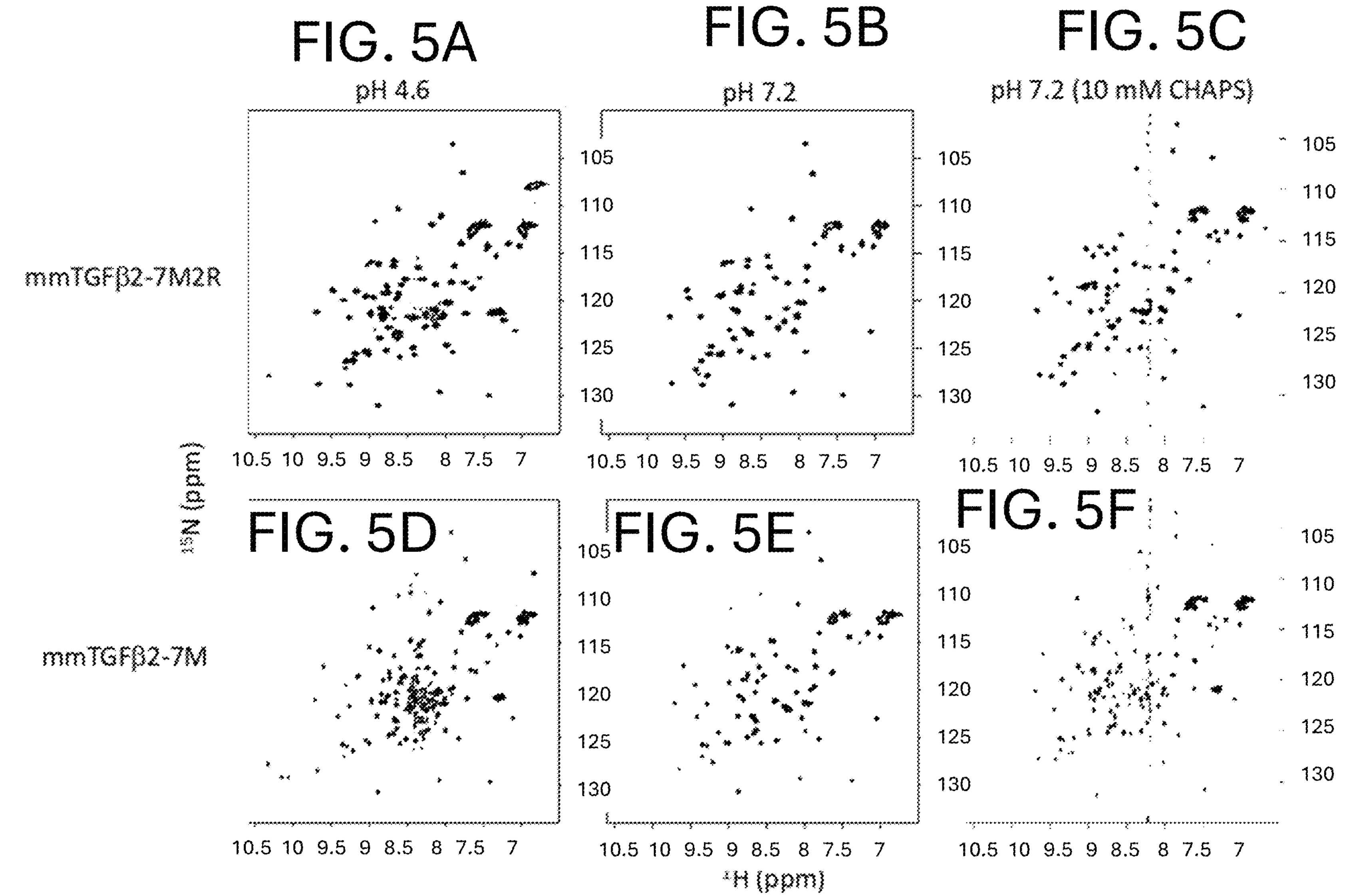
FIGS. 5A-5F: Amide $^1H$-$^{15}N$ one-bond shift correlation NMR spectra of mmTGF-β2-7M2R (FIGS. 5A-5C) compared to the parent protein, mmTGF-β2-7M (FIG. 5D-5F). Spectra were recorded at 37° C. in 10 mM phosphate buffer at pH 4.6 (FIGS. 5A and 5D) or pH 7.2, either in the absence of CHAPS in the buffer (FIGS. 5B and 5E) or with CHAPS added to a final concentration of 10 mM (FIGS. 5C and 5F).

Modifications to eliminate or reduce the propensity of mmTGF-β2-7M to aggregate were first investigated. Though it was previously shown that the engineered mmTGF-β2-7M monomer is much less prone to aggregate than wild type TGF-β2, mmTGF-β2-7M nonetheless retains some propensity to aggregate (Kim et al., *J Biol Chem* 292(17):7173-7188, 2017). This was evident from the appearance of the amide backbone $^{1}H$-$^{15}N$ signals, as detected by two-dimensional $^{1}H$-$^{15}N$ NMR shift correlation (HSQC, heteronuclear single-quantum correlation) spectrum when recorded either in the absence of the non-denaturing detergent 3-[(3-Cholamidopropyl)dimethylammonio]-1-propanesulfonate (CHAPS) (FIG. 5D, 5E) or in its presence (FIG. 5F). In the absence of CHAPS, the backbone amide signals were highly variable in intensity, with some barely detectable, particularly at pH 7.2 where the solubility of the protein is known to be reduced relative to that at pH 4.6. This type of variation in signal intensity is caused by the transient formation of higher order aggregates. The formation of such aggregates lengthens the rotational correlation time ($\tau_c$) of the protein, thus broadening the NMR signals and causing the signal intensities to decrease. It has been observed that the addition of increasing concentration of CHAPS at either pH 4.6 or 7.2 leads to the improvement in the intensities of many signals and thus an increase in the uniformity of these in the observed spectrum (FIG. 5F). The improvement in signal intensities was dependent on the concentration of CHAPS, with substantial improvements occurring up to concentrations of about 10 mM.

It was hypothesized that the role CHAPS played in reducing the aggregation of mmTGF-β2-7M may be due to transient formation of aggregates through some hydrophobic residues that remain in the region of the molecule, best described as the base of the fingers, which formerly in the wild TGF-β2 homodimer were part of the dimer interface (FIG. 4A). Though several substitutions were tested that were found to have little effect on aggregate formation, substitution of two residues in mmTGF-β2-7M to arginine—S57R and V59R (FIG. 4B) led to significantly reduced propensity to aggregate. This variant of mmTGF-β2-7M bearing the two resides replaced with arginine is designated as mmTGF-β2-7M2R (SEQ ID NO: 9). The evidence for reduced propensity to aggregate was the much more uniform NMR signal intensities that were observed for this variant, regardless of the pH or whether the non-denaturing CHAPS was added or not (FIGS. 5A-5C).

Modifications to Improve Folding

TFG-β proteins are formed from monomers that are classified as having a cystine knot growth factor fold (CKGF) (Hinck et al., *Cold Spring Harb Prospect Biol* 8(12):a022103, 2016). This fold is present in all proteins of the TGF-β family, but is also found in many other signaling proteins and signaling protein antagonists in humans. These include the signaling proteins platelet-derived growth factor (PDGF), vascular-endothelial growth factor (VEGF), and nerve growth factor (NGF) and antagonists, such as noggin, sclerostin, and protein related to Dan and Cerubus (PRDC). The proteins of the TFG-β family are unique among CKGF proteins in that they all have an N-terminal pro-domain. Though the roles of the pro-domains are still being investigated, it is known that they have a regulatory role for many proteins of the family (Hinck et al., *Cold Spring Harb Prospect Biol* 8(12):a022103, 2016). This regulation comes about from binding of the pro-domains to the growth factor domain (GFD), sometimes with sufficient (nanomolar to sub-nanomolar) affinity to completely block the ability of the GFD to bind the type I and type II receptors. Some pro-domains, such as those for TGF-β1, TGF-β2, and TGF-β3, only bind the GFD with very high affinity and thus maintain them in an inactive (latent) form until they are activated, but also are required for proper folding of the GFD. The GFDs of the TGF-βs, like that of other CKGF proteins, is characterized by a cystine knot, which is a structural motif stabilized by three disulfides (Schwarz, *Biol Chem* 398(12): 1295-1308, 2017). The three disulfides are very close in space to one another and thus their formation is complex and there are many possible alternative topological arrangements in addition to the correct one.

This is relevant to mmTFG-β2-7M since it retains the cystine knot as well as one additional disulfide, known as the 8-17 disulfide (corresponding to the cysteines at residues 7 and 16 relative to SEQ ID NO: 2). One way to produce mmTFG-β2-7M protein is to express it in bacteria in the form of insoluble inclusion bodies and refold the protein to form the native pairing of disulfides (Huang and Hinck, *Methods Mol Biol* 1344:63-92, 2016). The overall folding yields are nonetheless limited by aggregates that form as a result of mis-folding and improper pairing of its eight cysteine residues. mmTFG-β2-7M protein can also be produced by expressing the protein in a eukaryotic host as a secreted protein. This would cause the protein to transit the endoplasmic reticulum (ER) and Golgi, thus promoting folding by the endogenous disulfide-exchange and glycosylation machinery, as well as chaperones, that are inherent in eukaryotic cells to promote folding of disulfide-rich proteins. However, attempts at using this method for expression of mmTFG-β2-7M led to formation of misfolded disulfide linked aggregates. This likely occurred because mmTFG-β2-7M has been so dramatically modified relative wild type TFG-β that it would not be expected to bind and interact with its pro-domain.

Figures 6A, 6B, 6C:
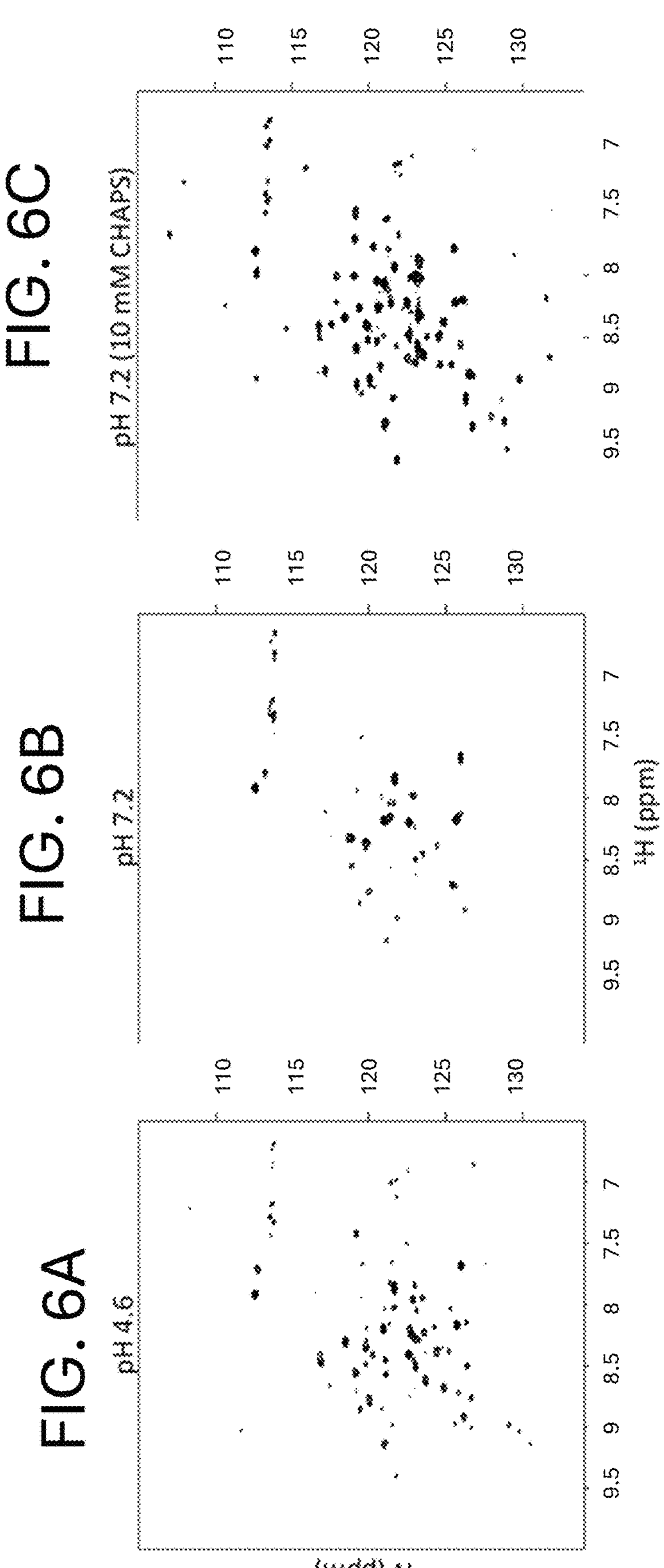
FIGS. 6A-6C: Amide $^1H$-$^{15}N$ one-bond shift correlation NMR spectra of mmTGF-β2-2M-De18-17. Spectra were recorded at 37° C. in 10 mM phosphate buffer at pH 4.6 (FIG. 6A), or pH 7.2, either in the absence of CHAPS in the buffer (FIG. 6B) or with CHAPS added to a final concentration of 10 mM (FIG. 6C).

Thus, modifications aimed at improving the folding of mmTGF-β2-7M were investigated. To improve the folding, each of the four disulfides of mmTGF-β2-7M were eliminated, one disulfide at a time. To do this, the two cysteines that form each disulfide were substituted with a valine-alanine pair and then the modified protein was expressed, refolded, and purified according to previous procedures (Kim et al., *J Biol Chem* 292(17):7173-7188, 2017). To enhance the likelihood of attaining natively folded protein, the substitutions were generated in the context of the engineered TGF-β2 monomer, but with just two essential residues changed to those of TGF-β1, instead of seven substitutions as in mmTGF-β2-7M. These variants were still expected to bind TβRII with high affinity, but fold with improved efficiency since TGF-β2 is known to fold with much greater efficiency than TGF-β1 (Huang and Hinck, *Methods Mol Biol* 1344:63-92, 2016). The results showed that in this background, the variant with the cysteines that form the 8-17 disulfide substituted with valine and alanine, designed as mmTGF-β2-2M-De18-17 (SEQ ID NO: FIG. 4C) was natively folded (FIGS. 6A-6C), but the variants with the other three disulfides eliminated 16-59, 45-90, and 49-92, were non-native. There is notably significant variation in NMR signal intensities in the absence of CHAPS, suggestive of aggregation, though these disparities are lessened upon addition of CHAPS (FIGS. 6A-6C). The fact that the 8-17 disulfide can be eliminated without disrupting the folding of the protein indicates that this could lead to significant improvements in folding, whether the protein is produced in bacteria and refolded in vitro, or if the protein in produced in eukaryotic cells as a secreted protein.

Figures 7A, 7B, 7C, 7D:
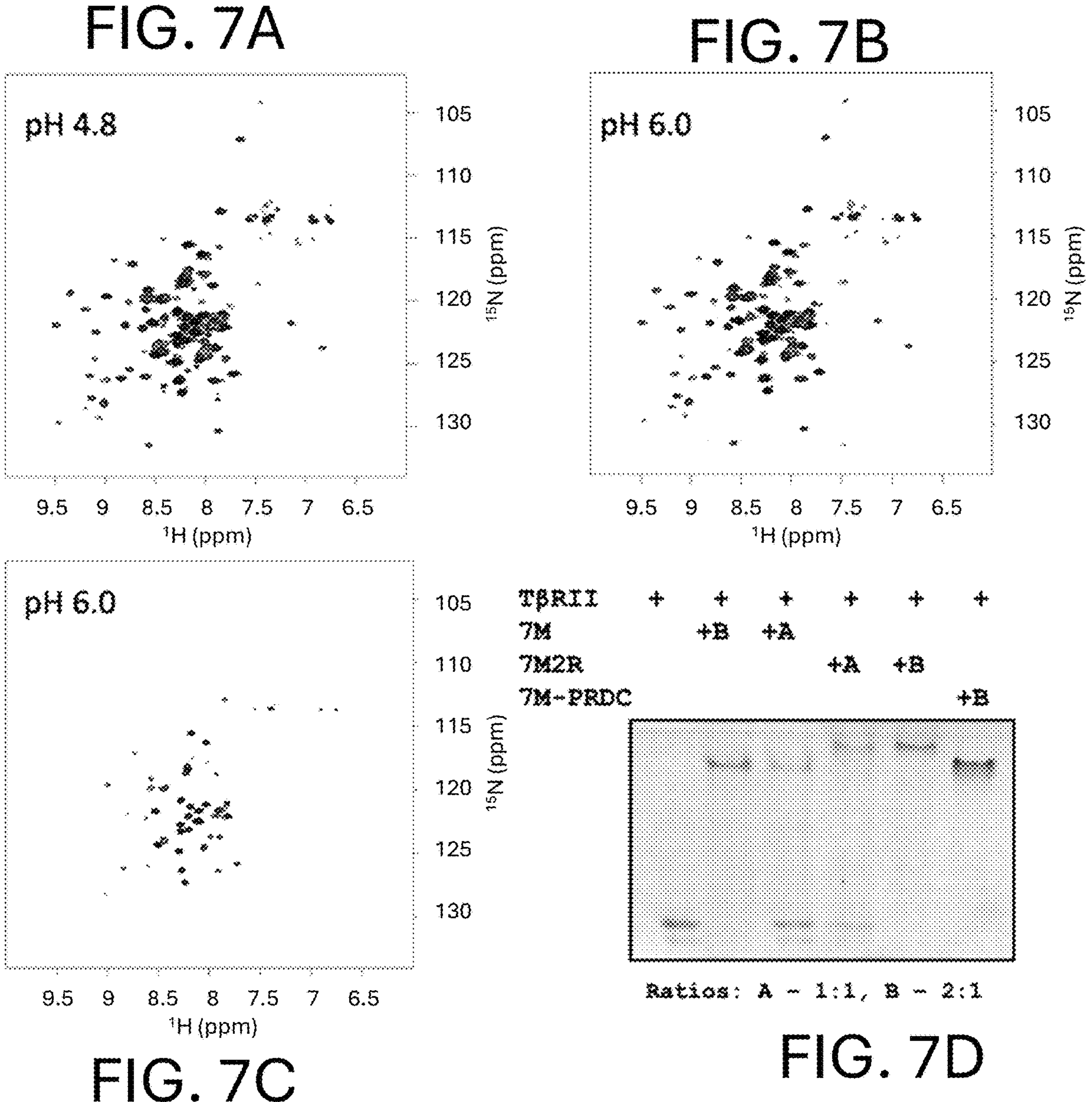
FIGS. 7A-7D: Amide $^1H$-$^{15}N$ one-bond shift correlation NMR spectra of mmTGF-β2-7M-PRDC (FIGS. 7A-7C) and binding to TβRII as detected by native gel electrophoresis (FIG. 7D). Spectra were recorded at 37° C. in 10 mM phosphate buffer at pH 4.8 (FIG. 7A) or pH 6.0 (FIGS. 7B-7C).

A third type of modification investigated was also aimed at improving the folding of mmTGF-β2-7M. The strategy chosen was to take advantage of the fact that there are some CKGF proteins, such as the bone morphogenetic protein (BMP) antagonist PRDC, that are produced naturally as monomers and do not have or rely upon a pro-domain for folding. To take advantage of the potential improvements in folding of PRDC, but to retain high affinity TβRII binding, a chimeric mmTGF-β2-7M:PRDC construct was generated in which the finger 1-2 and 3-4 regions of mmTGF-β2-7M, which are the regions responsible for binding TβRII, were grafted onto the cystine knot region of PRDC. This construct, designated as mmTGF-β2-7M-PRDC (SEQ ID NO: 11; FIG. 4D), was expressed in *E. coli*, refolded in a manner similar to that used for mmTGF-β27M (Kim et al., *J Biol Chem* 292(17):7173-7188, 2017), and purified to homogeneity using high-resolution cation exchange chromatography. Through NMR analysis, this protein was shown to be natively folded as evidenced by the dispersion of the amide signals well-outside of the random coil region, which corresponds to 7.9-8.5 ppm in the $^{1}$H dimension (FIGS. 7A-7C). This indicates that the design was successful, with the cystine knot region of PRDC being well-integrated with the finger region of mmTGF-β2-7M.

Binding Properties of mmTGF-β2-7M Variants

Figure 8:
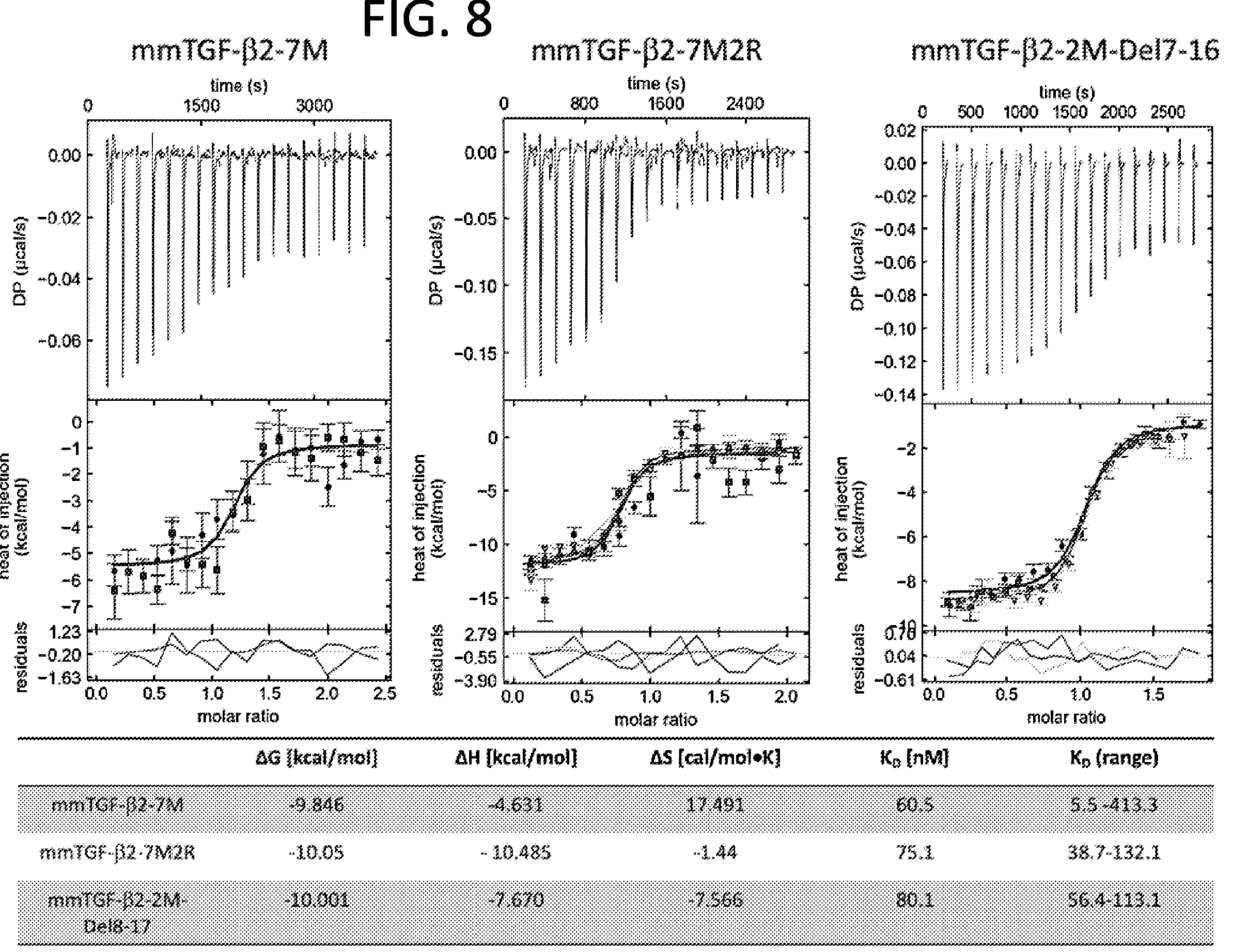
FIG. 8: Binding of the engineered TGF-beta monomers (mmTGF-β2-7M—left, mmTGF-β2-7M2R—middle, and mmTGF-β2-2M-De18-17—right) to the TGF-β type II receptor, TβRII, as detected by isothermal titration calorimetry (ITC). Upper panels depict the raw thermograms for three replicate titrations, while the lower panels depict the integrated heat (data points) for the three replicate titrations globally fit to a 1:1 binding isotherm (smooth line). Fitted parameters are provided in the Table at the bottom.

In order to be functional in cells and in vivo, a prerequisite of any designed mmTGF-β2-7M variant is that it bind TβRII with high-affinity. In order to evaluate the ability of the mmTGF-β2-7M variants described herein (mmTGF-β2-7M2R (SEQ ID NO: 9), mmTGF-β2-2M-De18-17 (SEQ ID NO: 10), and mmTGF-β2-7M-PRDC (SEQ ID NO: 11)) to bind TβRII, isothermal titration calorimetry (ITC) and native gels were used. The ITC binding experiments were performed by injecting increasing amounts of TβRII into mmTGF-β2-7M2R (SEQ ID NO: 9) or mmTGF-β2-2M-De18-17 (SEQ ID NO: 10), with mmTGF-β2-7M (SEQ ID NO: 7) used a reference control. These titrations yielded readily detectable isotherms with a large negative enthalpy and a near 1:1 binding stoichiometry (FIG. 8). The fits of the integrated heats to a 1:1 binding model yielded disassociation constants ($K_D$s) for binding TβRII of 75.1 nM and 80.1 nM for mmTGF-β2-7M2R and mmTGF-β2-2M-De18-17, respectively (FIG. 8). These K D s are within experimental error of that determined for mmTGF-β2-7M (60.5 nM) indicating that the substitutions introduced to reduce aggregation or improve folding had no deleterious effect on the ability of the protein to bind TβRII.

The binding of mmTGF-β2-7M-PRDC (SEQ ID NO: 11) was alternatively assessed using native gels. These do not provide a quantitative measurement of the $K_D$, though they are indicative of high affinity binding as detection of a complex requires that the two proteins remain bound on a timescale comparable to that of electrophoresis, which is on the order of an hour. The native gel showed that mmTGF-β2-7M, mmTGF-β2-7M2R, and mmTGF-β2-7M-PRDC all formed a band that migrates approximately one-fourth of the length of the gel, while TβRII runs over nearly the full-length of the gel (FIG. 7D). This, together with the previous finding that the mmTGF-β2-7M, mmTGF-β2-7M2R, and mmTGF-β2-7M-PRDC alone do not enter the gel, suggests that all three of these proteins bind TβRII with high affinity. This is consistent with the ITC results for the mmTGF-β2-7M and mmTGF-β2-7M2R variants, and indicates that this also true for mmTGF-β2-7M-PRDC.

Inhibitory Properties of mmTGF-β2-7M Variants

In order to be functional in vivo, any designed mmTGF-β2-7M variant should inhibit TGF-β signaling in cells. In order to assess this for the disclosed mmTGF-β2-7M variants, mmTGF-β2-7M2R (SEQ ID NO: 9), mmTGF-β2-2M-De18-17 (SEQ ID NO: 10), and mmTGF-β2-7M-PRDC (SEQ ID NO: 11), an HEK-293 TGF-β luciferase reporter cell line in which the cells are stably transfected with a TGF-β CAGA enhancer element fused to a luciferase reporter gene was used. To assess inhibitory potential with this assay, the cells were plated in 96-well plates and varying concentrations of mmTGF-β2-7M2R, mmTGF-β2-2M-De18-17, and mmTGF-β2-7M-PRDC were added, with mmTGF-β2-7M used as a control. After 30 minutes, TGF-β signaling was stimulated by adding TGF-β3 to a final concentration of 10 pM and after 12 hours, the cells were lysed and the luciferase activity was assessed. The results obtained showed that mmTGF-β2-7M2R, mmTGF-β2-2M-De18-17, and mmTGF-β2-7M-PRDC each potently inhibited signaling induced by TGF-β3, with fitted $IC_{50}$ values of 53 nM, 111 nM, and 283 nM, respectively. The values for mmTGF-β2-7M2R and mmTGF-β2-2M-De18-17 were both within a factor of two of that measured for mmTGF-β2-7M, indicating that both of these proteins are nearly as effective as mmTGF-β2-7M ($IC_{50}$ 58 nM). While still potent, the $IC_{50}$ for mmTGF-β2-7M-PRDC is 283 nM, which is about 5-fold reduced relative to mmTGF-β2-7M. This indicates that although mmTGF-β2-7M-PRDC is a functional TGF-β inhibitor, its potency may be compromised slightly due to some small changes in the orientations of the two finger regions.

SUMMARY

The mmTGF-β2-7M variants disclosed herein harbor substitutions that reduce their propensity to aggregate and increase their propensity to fold. The mmTGF-β2-7M variants were each shown to retain the ability to bind TβRII with high affinity and to potently inhibit TGF-β3 signaling in cultured cells. Therefore, the disclosed mmTGF-β2-7M variants possess attributes that improve their ability to be administered in vivo and thus provide new avenues for therapeutically intervening to attenuate TGF-β mediated disease progression.

Example 7

Oncolytic Vaccinia Virus Expressing a mmTGF-β2 Variant Exhibits Superior Efficacy in Resistant Cancer Models Vaccinia virus (VV) expressing the mmTGFβ2 variant mmTGF-β2-7M2R-De18-17 (SEQ ID NO: 12) (also referred to as "variant 1" or "var 1") was tested in two resistant cancer models. The first model is a head and neck squamous cell carcinoma (HNSCC) cell line, MEER subclone (HPV+HNSCC), which is resistant to oncolytic virus therapy. The second model is a melanoma cell line, clone 24 (CL24 melanoma; Pten-deficient $Braf^{V600E}$), which does not respond to immunotherapies such as oncolytic virus or anti-PD1.

Figure 10A:
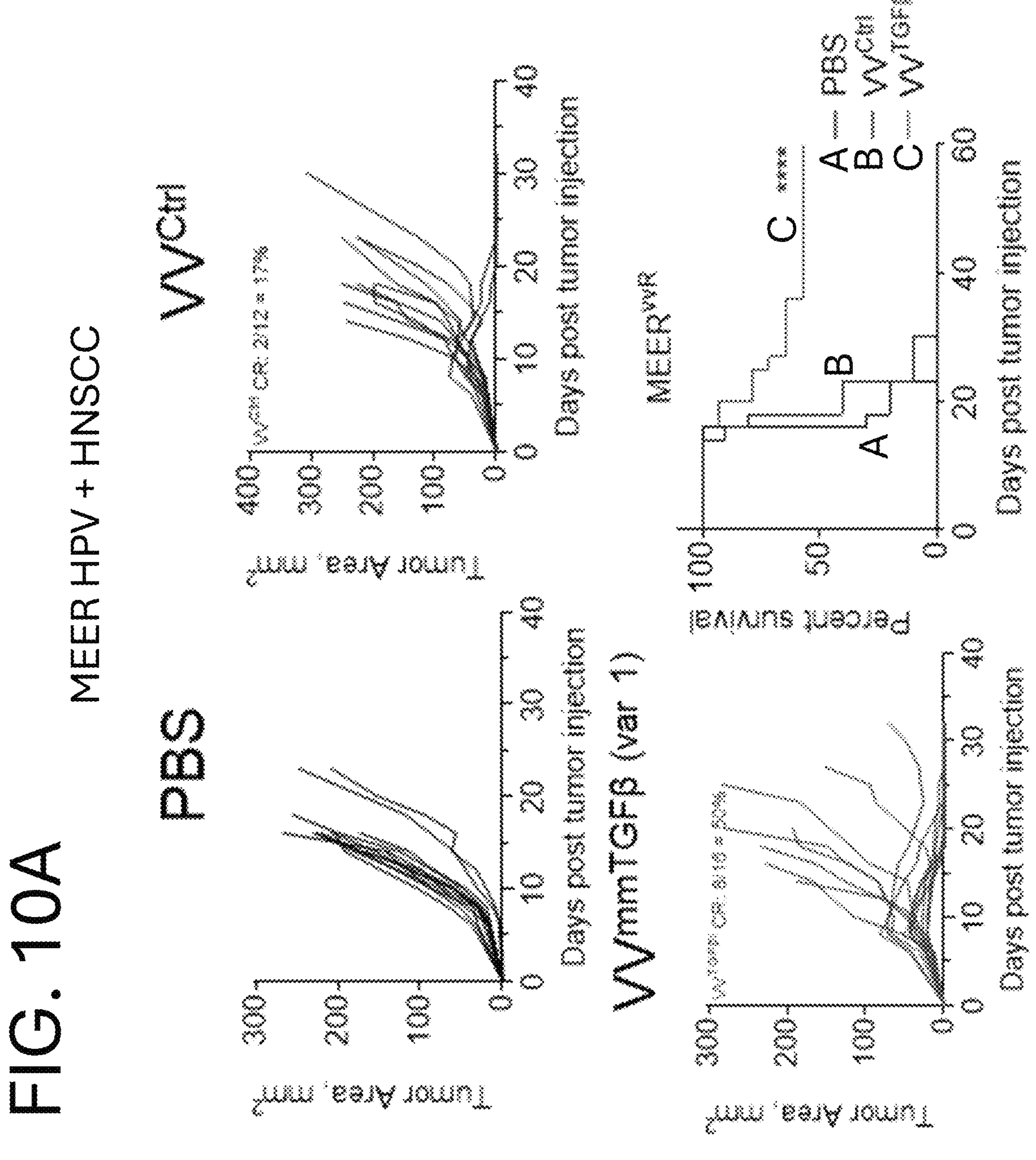
FIGS. 10A-10C: Vaccinia virus (VV) expressing mmTGFβ variant 1 (mmTGF-β2-7M2R-De18-17) exhibits superior efficacy in resistant cancer models.

In a first study, C57/BL6J mice were inoculated with $1\times10^5$ MEER cells subcutaneously and after seven days, mice received an intratumoral injection of $2.5\times10^5$ PFU of either control VV or VV engineered to express mmTGF-β2-7M2R-De18-17 ($VV^{mmTGF\beta(var\ 1)}$) (SEQ ID NO: 12). As shown in FIG. 10A, the control virus had a modest curative effect, whereas half of the mice treated with $VV^{mmTGF\beta(var\ 1)}$ exhibited a complete response and a long lasting survival benefit.

Figure 10B:
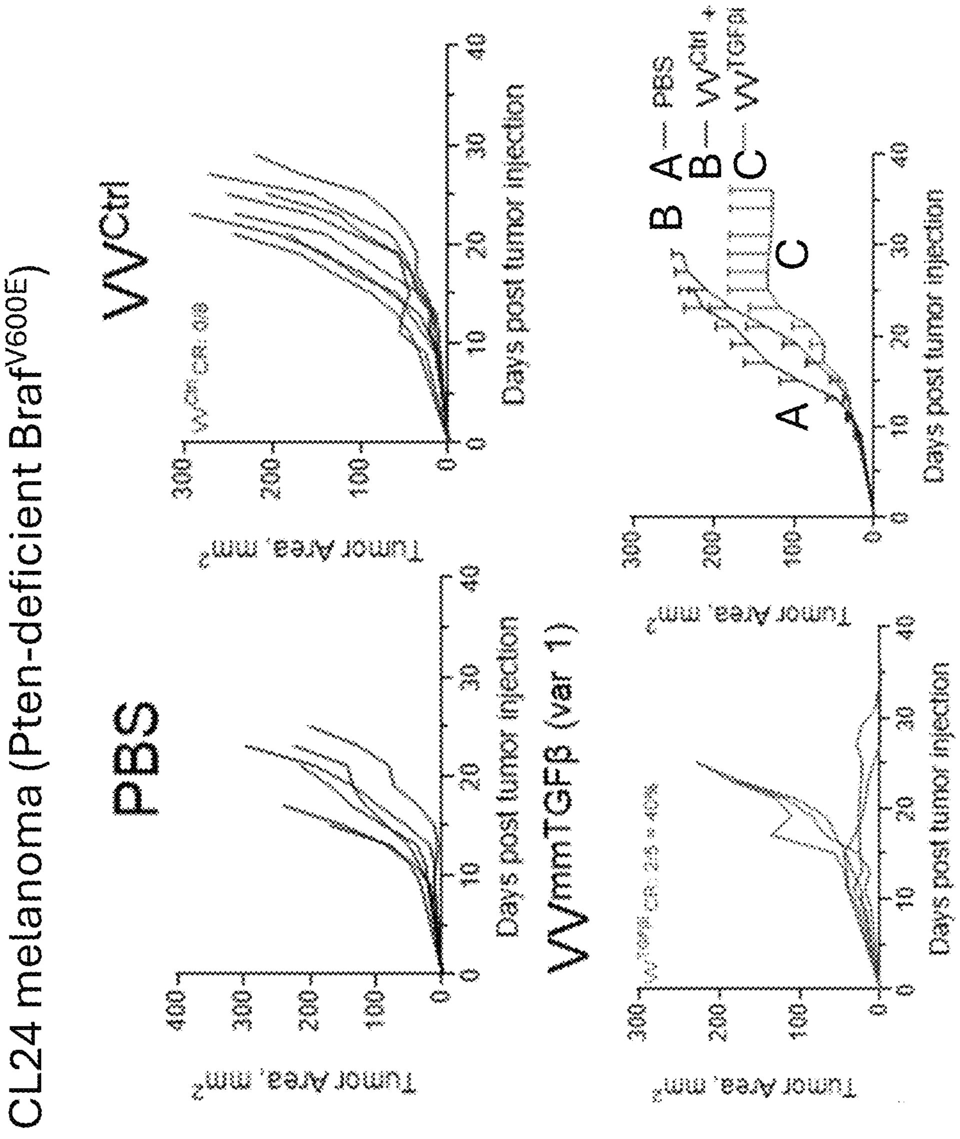
Figure 10C:
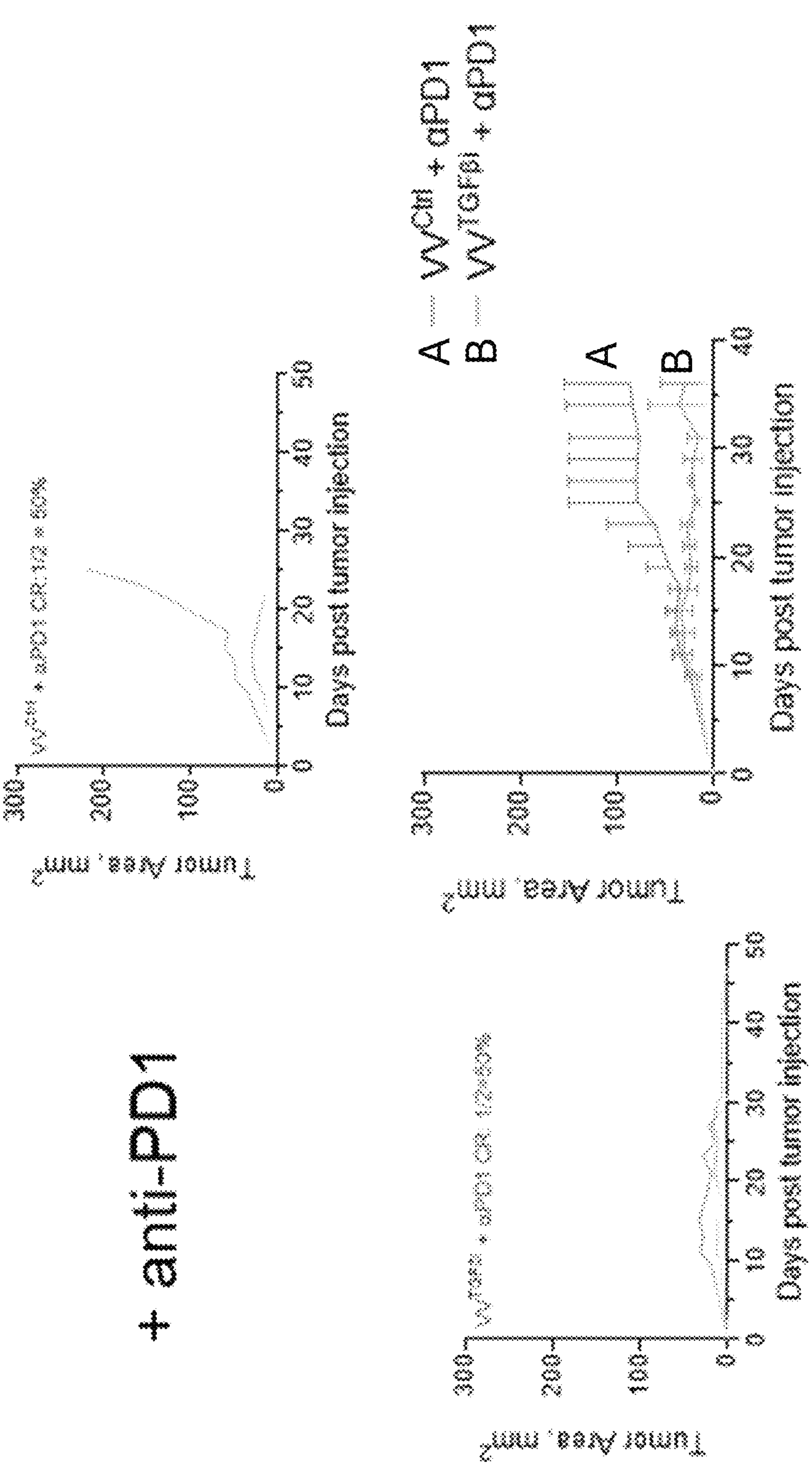

In a second study, C57/BL6J mice were inoculated with $1\times10^5$ CL24 cells intradermally and after seven days, mice received $2.5\times10^5$ PFU of VV control or $VV^{mmTGF\beta(var\ 1)}$. As shown in FIG. 10B, targeting TGFβ led to complete response rates in 40% of animals in this aggressive model of melanoma. Addition of anti-PD1 enhanced the tumor inhibition effect in the CL24 model (FIG. 10C), leading to significant synergy between VV, anti-PD1, and inhibition of TGFβ.

In view of the many possible embodiments to which the principles of the disclosed subject matter may be applied, it should be recognized that the illustrated embodiments are only examples of the disclosure and should not be taken as limiting the scope of the disclosure. Rather, the scope of the disclosure is defined by the following claims. We therefore claim all that comes within the scope and spirit of these claims.

The invention claimed is:

1. An oncolytic virus encoding a human recombinant transforming growth factor (TGF)-β monomer, wherein the human TGF-β monomer comprises:

a leucine to arginine substitution at an amino acid residue corresponding to residue 51 of SEQ ID NO: 2;

an alanine to lysine substitution at an amino acid residue corresponding to residue 74 of SEQ ID NO: 2;

a cysteine to serine or a cysteine to arginine substitution at an amino acid residue corresponding to residue 77 of human TGF-β2 set forth as SEQ ID NO: 2; and a deletion of the α3 helix corresponding to amino acid residues 52-71 of human TGF-β2 set forth as SEQ ID NO: 2.

2. The oncolytic virus of claim 1, wherein the human TGF-β monomer is a human TGF-β2 monomer comprising at least one amino acid substitution that increases affinity of the monomer for TGF-β receptor II (TβRII), wherein the at least one amino acid substitution that increases affinity of the monomer for TβRII comprises:

a lysine to arginine substitution at an amino acid residue corresponding to residue 25 of SEO ID NO: 2:

an arginine to lysine substitution at an amino acid residue corresponding to residue 26 of SEQ ID NO: 2:

a leucine to valine substitution at an amino acid residue corresponding to residue 89 of SEQ ID NO: 2:

an isoleucine to valine substitution at an amino acid residue corresponding to residue 92 of SEO ID NO: 2:

a lysine to arginine substitution at an amino acid residue corresponding to residue 94 of SEO ID NO: 2:

a threonine to lysine substitution at an amino acid residue corresponding to residue 95 of SEO ID NO: 2; and/or an isoleucine to valine substitution at an amino acid residue corresponding to residue 98 of SEQ ID NO: 2.

3. The oncolytic virus of claim 1, wherein the human TGF-β monomer is a human TGF-β2 comprising:

a cysteine to serine substitution at an amino acid residue corresponding to residue 77 of human TGF-β2 set forth as SEQ ID NO: 2;

a deletion of the 3 helix corresponding to amino acid residues 52-71 of human TGF-β2 set forth as SEQ ID NO: 2;

a lysine to arginine substitution at an amino acid residue corresponding to residue 25 of SEQ ID NO: 2;

an arginine to lysine substitution at an amino acid residue corresponding to residue 26 of SEQ ID NO: 2;

a leucine to arginine substitution at an amino acid residue corresponding to residue 51 of SEQ ID NO: 2;

an alanine to lysine substitution at an amino acid residue corresponding to residue 74 of SEQ ID NO: 2;

a leucine to valine substitution at an amino acid residue corresponding to residue 89 of SEQ ID NO: 2;

an isoleucine to valine substitution at an amino acid residue corresponding to residue 92 of SEQ ID NO: 2;

a lysine to arginine substitution at an amino acid residue corresponding to residue 94 of SEQ ID NO: 2;

a threonine to lysine substitution at an amino acid residue corresponding to residue 95 of SEQ ID NO: 2; and an isoleucine to valine substitution at an amino acid residue corresponding to residue 98 of SEQ ID NO: 2.

4. The oncolytic virus of claim 3, wherein the amino acid sequence of the human TGF-β2 monomer comprises or consists of SEQ ID NO: 7.

5. The oncolytic virus of claim 1, wherein the human TGF-β monomer is a human TGF-β2 monomer comprising:

a deletion of the α3 helix corresponding to amino acid residues 52-71 of human TGF-β2 set forth as SEQ ID NO: 2;

a lysine to arginine substitution at an amino acid residue corresponding to residue 25 of SEQ ID NO: 2;

an arginine to lysine substitution at an amino acid residue corresponding to residue 26 of SEQ ID NO: 2;

a leucine to arginine substitution at an amino acid residue corresponding to residue 51 of SEQ ID NO: 2;

an alanine to lysine substitution at an amino acid residue corresponding to residue 74 of SEQ ID NO: 2;

a cysteine to arginine substitution at an amino acid residue corresponding to residue 77 of SEQ ID NO: 2;

a valine to arginine substitution at an amino acid residue corresponding to residue 79 of SEQ ID NO: 2;

a leucine to valine substitution at an amino acid residue corresponding to residue 89 of SEQ ID NO: 2;

an isoleucine to valine substitution at an amino acid residue corresponding to residue 92 of SEQ ID NO: 2;

a lysine to arginine substitution at an amino acid residue corresponding to residue 94 of SEQ ID NO: 2;

a threonine to lysine substitution at an amino acid residue corresponding to residue 95 of SEQ ID NO: 2; and an isoleucine to valine substitution at an amino acid residue corresponding to residue 98 of SEQ ID NO: 2.

6. The oncolytic virus of claim 5, wherein the amino acid sequence of the human TGF-β2 monomer comprises or consists of SEQ ID NO: 9.

7. The oncolytic virus of claim 1, wherein the human TGF-β monomer is a human TGF-β2 monomer comprising:

a cysteine to serine substitution at an amino acid residue corresponding to residue 77 of SEQ ID NO: 2;

a deletion of the α3 helix corresponding to amino acid residues 52-71 of human TGF-β2 set forth as SEQ ID NO: 2;

a cysteine to valine substitution at an amino acid residue corresponding to residue 7 of SEQ ID NO: 2;

a cysteine to alanine substitution at an amino acid residue corresponding to residue 16 of SEQ ID NO: 2;

a lysine to arginine substitution at an amino acid residue corresponding to residue 25 of SEQ ID NO: 2;

a leucine to arginine substitution at an amino acid residue corresponding to residue 51 of SEQ ID NO: 2;

an alanine to lysine substitution at an amino acid residue corresponding to residue 74 of SEQ ID NO: 2; and a lysine to arginine substitution at an amino acid residue corresponding to residue 94 of SEQ ID NO: 2.

8. The oncolytic virus of claim 7, wherein the amino acid sequence of the human TGF-β2 monomer comprises or consists of SEQ ID NO: 10.

9. The oncolytic virus of claim 1, wherein the TGF-β monomer is a human TGF-β2 monomer comprising:

a deletion of the α3 helix corresponding to amino acid residues 52-71 of human TGF-β2 set forth as SEQ ID NO: 2;

a cysteine to valine substitution at an amino acid residue corresponding to residue 7 of SEQ ID NO: 2;

a cysteine to alanine substitution at an amino acid residue corresponding to residue 16 of SEQ ID NO: 2;

a lysine to arginine substitution at an amino acid residue corresponding to residue 25 of SEQ ID NO: 2;

an arginine to lysine substitution at an amino acid residue corresponding to residue 26 of SEQ ID NO: 2;

a leucine to arginine substitution at an amino acid residue corresponding to residue 51 of SEQ ID NO: 2;

an alanine to lysine substitution at an amino acid residue corresponding to residue 74 of SEQ ID NO: 2;

a cysteine to arginine substitution at an amino acid residue corresponding to residue 77 of SEQ ID NO: 2;

a valine to arginine substitution at an amino acid residue corresponding to residue 79 of SEQ ID NO: 2;

a leucine to valine substitution at an amino acid residue corresponding to residue 89 of SEQ ID NO: 2;

an isoleucine to valine substitution at an amino acid residue corresponding to residue 92 of SEQ ID NO: 2;

a lysine to arginine substitution at an amino acid residue corresponding to residue 94 of SEQ ID NO: 2;

a threonine to lysine substitution at an amino acid residue corresponding to residue 95 of SEQ ID NO: 2; and an isoleucine to valine substitution at an amino acid residue corresponding to residue 98 of SEQ ID NO: 2.

10. The oncolytic virus of claim 8, wherein the amino acid sequence of the human TGF-β2 monomer comprises or consists of SEQ ID NO: 12.

11. The oncolytic virus of claim 1, wherein the human TGF-β monomer is a human TGF-β1 monomer or a human TGF-β3 monomer.

12. The oncolytic virus of claim 11, wherein the human TGF-β1 monomer further comprises:

an isoleucine to arginine substitution at an amino acid residue corresponding to residue 52 of SEQ ID NO: 1;

an alanine to lysine substitution at an amino acid residue corresponding to residue 74 of SEQ ID NO: 1;

an alanine to serine substitution at an amino acid residue corresponding to residue 75 of SEQ ID NO: 1; or an isoleucine to arginine substitution at an amino acid residue corresponding to residue 52, an alanine to lysine substitution at an amino acid residue corresponding to residue 74 and an alanine to serine substitution at an amino acid residue corresponding to residue 75 of SEQ ID NO: 1.

13. The oncolytic virus of claim 12, wherein the amino acid sequence of the human TGF-β1 monomer comprises or consists of SEQ ID NO: 4.

14. The oncolytic virus of claim 11, wherein the human TGF-β3 monomer further comprises:

a leucine to glutamate substitution at an amino acid residue corresponding to residue 51 of SEQ ID NO: 3;

an alanine to glutamate substitution at an amino acid residue corresponding to residue 72 of SEQ ID NO: 3;

an alanine to aspartate substitution at an amino acid residue corresponding to residue 74 of SEQ ID NO: 3; or a leucine to glutamate substitution at an amino acid residue corresponding to residue 51, an alanine to glutamate substitution at an amino acid residue corresponding to residue 72 and an alanine to aspartate substitution at an amino acid residue corresponding to residue 74 of SEQ ID NO: 3.

15. The oncolytic virus of claim 14, wherein the amino acid sequence of the human TGF-β3 monomer comprises or consists of SEQ ID NO: 6.

16. The oncolytic virus of claim 1, wherein the TGF-β monomer further comprises a signal sequence.

17. The oncolytic virus of claim 1, wherein the virus is a vaccinia virus, a herpes simplex virus, or an adenovirus.

18. The oncolytic virus of claim 17, wherein the vaccinia virus comprises a modification of the gene encoding thymidine kinase (TK) and a modification of the gene encoding virus growth factor (VGF).

19. The oncolytic virus of claim 18, wherein the modification of the gene encoding TK comprises a complete or partial deletion of the gene and/or the modification of the gene encoding VGF comprises a complete or partial deletion of the gene.

20. A composition comprising the oncolytic virus of claim 1 and a pharmaceutically acceptable carrier.

21. A method of treating cancer in a subject, comprising administering to the subject a therapeutically effective amount of the composition of claim 20.

22. A method of inhibiting tumor growth or tumor metastasis in a subject with cancer, comprising administering to the subject a therapeutically effective amount of the composition of claim 20.

23. The method of claim 21, wherein the cancer is melanoma, head and neck cancer, or pancreatic cancer.

* * * * *

SEQUENCE LISTING

```
<160> NUMBER OF SEQ ID NOS: 12

<210> SEQ ID NO 1
<211> LENGTH: 112
<212> TYPE: PRT
<213> ORGANISM: Homo sapiens

<400> SEQUENCE: 1

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110


<210> SEQ ID NO 2
<211> LENGTH: 112
<212> TYPE: PRT
<213> ORGANISM: Homo sapiens

<400> SEQUENCE: 2

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45
```

```
Pro Tyr Leu Trp Ser Ser Asp Thr Gln His Ser Lys Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110


<210> SEQ ID NO 3
<211> LENGTH: 112
<212> TYPE: PRT
<213> ORGANISM: Homo sapiens

<400> SEQUENCE: 3

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110


<210> SEQ ID NO 4
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 4

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Arg Ala Ser Lys Ser Pro Ser Cys Val Pro Gln Ala Leu Glu
    50                  55                  60

Pro Leu Pro Ile Val Tyr Tyr Val Gly Arg Lys Pro Lys Val Glu Gln
65                  70                  75                  80

Leu Ser Asn Met Ile Val Arg Ser Cys Lys Cys Ser
                85                  90


<210> SEQ ID NO 5
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 5
```

```
Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Arg Ala Ser Lys Ser Pro Ser Cys Val Ser Gln Asp Leu Glu
    50                  55                  60

Pro Leu Thr Ile Leu Tyr Tyr Ile Gly Lys Thr Pro Lys Ile Glu Gln
65                  70                  75                  80

Leu Ser Asn Met Ile Val Lys Ser Cys Lys Cys Ser
                85                  90


<210> SEQ ID NO 6
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 6

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Glu Glu Ser Asp Ser Pro Ser Cys Val Pro Gln Asp Leu Glu
    50                  55                  60

Pro Leu Thr Ile Leu Tyr Tyr Val Gly Arg Thr Pro Lys Val Glu Gln
65                  70                  75                  80

Leu Ser Asn Met Val Val Lys Ser Cys Lys Cys Ser
                85                  90


<210> SEQ ID NO 7
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 7

Ala Leu Asp Ala Ala Tyr Cys Phe Arg Asn Val Gln Asp Asn Cys Cys
1               5                   10                  15

Leu Arg Pro Leu Tyr Ile Asp Phe Arg Lys Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Arg Ala Ser Lys Ser Pro Ser Cys Val Ser Gln Asp Leu Glu
    50                  55                  60

Pro Leu Thr Ile Val Tyr Tyr Val Gly Arg Lys Pro Lys Val Glu Gln
65                  70                  75                  80

Leu Ser Asn Met Ile Val Lys Ser Cys Lys Cys Ser
                85                  90


<210> SEQ ID NO 8
<211> LENGTH: 20
<212> TYPE: PRT
<213> ORGANISM: Artificial Sequence
```

<220> FEATURE:
<223> OTHER INFORMATION: Synthetic polypeptide

<400> SEQUENCE: 8

Met Tyr Arg Met Gln Leu Leu Ser Cys Ile Ala Leu Ser Leu Ala Leu
1 5 10 15

Val Thr Asn Ser
20

<210> SEQ ID NO 9
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 9

Ala Leu Asp Ala Ala Tyr Cys Phe Arg Asn Val Gln Asp Asn Cys Cys
1 5 10 15

Leu Arg Pro Leu Tyr Ile Asp Phe Arg Lys Asp Leu Gly Trp Lys Trp
20 25 30

Ile His Glu Pro Lys Gly Tyr Asn Ala Asn Phe Cys Ala Gly Ala Cys
35 40 45

Pro Tyr Arg Ala Ser Lys Ser Pro Arg Cys Arg Ser Gln Asp Leu Glu
50 55 60

Pro Leu Thr Ile Val Tyr Tyr Val Gly Arg Lys Pro Lys Val Glu Gln
65 70 75 80

Leu Ser Asn Met Ile Val Lys Ser Cys Lys Cys Ser
85 90

<210> SEQ ID NO 10
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 10

Ala Leu Asp Ala Ala Tyr Val Phe Arg Asn Val Gln Asp Asn Cys Ala
1 5 10 15

Leu Arg Pro Leu Tyr Ile Asp Phe Arg Arg Asp Leu Gly Trp Lys Trp
20 25 30

Ile His Glu Pro Lys Gly Tyr Asn Ala Asn Phe Cys Ala Gly Ala Cys
35 40 45

Pro Tyr Arg Ala Ser Lys Ser Pro Ser Cys Val Ser Gln Asp Leu Glu
50 55 60

Pro Leu Thr Ile Leu Tyr Tyr Ile Gly Arg Thr Pro Lys Ile Glu Gln
65 70 75 80

Leu Ser Asn Met Ile Val Lys Ser Cys Lys Cys Ser
85 90

<210> SEQ ID NO 11
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 11

Lys Glu Val Leu Ala Ser Ser Gln Glu Ala Leu Val Val Thr Glu Arg
1 5 10 15

-continued

```
Lys Tyr Leu Lys Ser Asp Trp Cys Lys Leu Arg Pro Leu Tyr Ile Asp
            20                  25                  30

Phe Arg Lys Asp Leu Gly Trp Lys Trp Ile His Glu Pro Lys Gly Tyr
        35                  40                  45

Asn Ala Asn Phe Cys Tyr Gly Gln Cys Asn Ser Phe Tyr Ile Pro Arg
    50                  55                  60

His Val Lys Lys Glu Glu Asp Ser Phe Gln Ser Ser Ala Phe Cys Val
65                  70                  75                  80

Ser Gln Asp Leu Glu Pro Leu Thr Ile Val Tyr Tyr Val Gly Arg Lys
                85                  90                  95

Pro Lys Val Glu Gln Leu Ser Asn Met Ile Val Lys Ser Cys Arg Cys
            100                 105                 110

Met Ser Val
        115


<210> SEQ ID NO 12
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 12

Ala Leu Asp Ala Ala Tyr Val Phe Arg Asn Val Gln Asp Asn Cys Ala
1               5                   10                  15

Leu Arg Pro Leu Tyr Ile Asp Phe Arg Lys Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Arg Ala Ser Lys Ser Pro Arg Cys Arg Ser Gln Asp Leu Glu
    50                  55                  60

Pro Leu Thr Ile Val Tyr Tyr Val Gly Arg Lys Pro Lys Val Glu Gln
65                  70                  75                  80

Leu Ser Asn Met Ile Val Lys Ser Cys Lys Cys Ser
                85                  90
```